US007411113B2

(12) United States Patent
Liebergesell et al.

(10) Patent No.: US 7,411,113 B2
(45) Date of Patent: Aug. 12, 2008

(54) **MODULATING *MYO*-INOSITOL CATABOLISM IN PLANTS**

(75) Inventors: Matthias Liebergesell, West Des Moines, IA (US); Jinrui Shi, Johnston, IA (US); George W. Singletary, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 110 days.

(21) Appl. No.: 11/064,295

(22) Filed: Feb. 23, 2005

(65) Prior Publication Data

US 2006/0064779 A1 Mar. 23, 2006

Related U.S. Application Data

(60) Provisional application No. 60/547,640, filed on Feb. 25, 2004.

(51) Int. Cl.
*A01H 5/00* (2006.01)
*C07H 21/04* (2006.01)
*C12N 15/63* (2006.01)
*C12N 5/14* (2006.01)

(52) U.S. Cl. .................. 800/295; 536/23.1; 435/320.1; 435/419; 435/468; 800/320.1

(58) Field of Classification Search ................. 800/278; 536/23.1; 435/419, 468
See application file for complete search history.

(56) References Cited

U.S. PATENT DOCUMENTS

| 5,689,054 | A | 11/1997 | Raboy |
| 6,197,561 | B1 | 3/2001 | Martino-Catt et al. |
| 6,291,224 | B1 | 9/2001 | Martino-Catt et al. |
| 2003/0009011 | A1 | 1/2003 | Shi et al. |
| 2003/0079247 | A1 | 4/2003 | Shi et al. |
| 2004/0034888 | A1 | 2/2004 | Liu et al. |
| 2004/0214272 | A1* | 10/2004 | La Rosa et al. ............ 435/69.1 |
| 2004/0216190 | A1 | 10/2004 | Kovalic |
| 2006/0123505 | A1* | 6/2006 | Kikuchi et al. .............. 800/278 |
| 2006/0150283 | A1* | 7/2006 | Alexandrov et al. ........ 800/288 |

FOREIGN PATENT DOCUMENTS

| EP | 1033405 A2 * | 9/2000 |
| WO | WO 99/05298 A1 | 2/1999 |
| WO | WO 99/07211 A1 | 2/1999 |
| WO | WO 99/55879 A1 | 11/1999 |
| WO | WO 02/059324 A2 | 8/2002 |
| WO | WO 03/027243 A2 | 4/2003 |
| WO | WO 2005/078079 A1 | 8/2005 |

OTHER PUBLICATIONS

Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
Elomaa et al. (Molecular Breeding, 2:41-50, 1996).*
Colliver et al. (Plant molecular Biology, 35:509-522, 1997).*
Arner, R.J., et al., *myo*-Inositol Oxygenase: Molecular Cloning and Expression of a Unique Enzyme that Oxidizes *myo*=Inositol and D-Chiro-Inositol, *Biochem. J.*, 2001, pp. 313-320, vol. 360.
Bollmann, O., et al., "The Enzymes Involved in the Synthesis of Phytic Acid in *Lemna Gibba* (Studies on the Biosynthesis of Cyclitols, XL)," *Molecular & Cellular Biochemistry*, 1980, pp. 171-175, vol. 30(3).
Falcon-Perez, J. M., et al., "Functional Domain analysis of the Yeast ABC Transporter Yef1p by Site-directed Mutagenesis," *J. Biol. Chem.*, Aug. 13, 1999, pp. 23584-23590, vol. 274, No. 33.
Hitz, W.D., et al., "Biochemical and Molecular Characterization of a Mutation That Confers a Decreased Raffinosaccharide and Phytic Acid Phenotype on Soybean Seeds," *Plant Physiol.*, Feb. 2002, pp. 650-660, vol. 128.
Koller, E., et al., "*Myo*-Inositol Oxygenase from Oat Seedlings," *Molecular & Cellular Biochemistry*, Jan. 31, 1976, pp. 33-39, vol. 10, No. 1.
Loewus, M.W., et al., "Enantiomeric Form of *myo*-Inositol-1-Phosphate Produced by *myo*-Inositol-1-phosphate Synthase and *myo*-Inositol Kinase in Higher Plants," *Plant Physiol*, 1982, pp. 1661-1663, vol. 70.
Loewus, F.A., and P.P.N. Murthy, "*myo*-Inositol Metabolism in Plants," *Plant Science*, 2000, pp. 1-19, vol. 150(1).
Raboy, V., et al., "Origin and Seed Phenotype of Maize *low phytic acid* 1-1 and *low phytic acid* 2-1," *Plant Physiol.*, Sep. 2000, pp. 355-368, vol. 124.

(Continued)

*Primary Examiner*—Phuong T Bui
*Assistant Examiner*—Vinod Kumar
(74) *Attorney, Agent, or Firm*—Alston & Bird LLP

(57) ABSTRACT

Compositions and methods for modulating MIOX activity are provided. Such compositions include nucleotide sequences for novel MIOX sequences obtained from maize, amino acid sequences for the proteins encoded by the nucleotide sequences of the invention, and variants and fragments thereof. Methods of the invention involve introducing into a plant a nucleotide construct comprising a MIOX nucleotide sequence operably linked to a promoter that drives expression in a plant. Expression of the novel nucleotide sequences disclosed herein confers advantageous agronomic properties on a plant. Transformed plants, plant cells, and seeds are additionally provided.

11 Claims, 14 Drawing Sheets

OTHER PUBLICATIONS

Shi, J., et al., "The Maize Low-Phytic Acid Mutant *lpa2* is Caused by Mutation in an Inositol Phosphate Kinase Gene," *Plant Physiology*, 2003, pp. 507-515, vol. 131(2), American Society of Plant Biologists, USA.

Shi, J., et al., "The Maize *low-phytic acid* 3 Encodes a *Myo*-inositol Kinase That Plays a Role in Phytic Acid Biosynthesis in Developing Seeds," *The Plant Journal*, 2005, pp. 708-719, vol. 42.

Stein, A.J., and J.H. Geiger, "The Crystal Structure and Mechanism of 1-L-*myo*-Inositol-1-phosphate Synthase," *J. Biol. Chem.*, Mar. 15, 2002, pp. 9484-9491, vol. 227, No. 11.

NCBI Database Report for Accession No. AF323175, Direct Submission on Nov. 21, 2000.

* cited by examiner

Figure 1

Domain A:
(L/M)L(N/D)X(F/L)(V/I)D(E/D)SDPD(L/V)DXP(Q/N)(I/S)XH(L/A)(F/L)Q(T/S)AEXIRKXXP(D/N)(E/K)DW(L/F)HL(T/V)(A/G)L(L/I)HDLGK(V/I)(L/M) (SEQ ID NO:20)

Domain B:
PQWAVVGDTFP(V/L)GC (SEQ ID NO:21)

Domain C:
CG(L/V)(D/E)N(V/I)(L/V)MSWGHD(D/E)Y(M/L)Y (SEQ ID NO:22)

Domain D:
(L/F)(F/Y)(M/I)IR(Y/F)HSFYPXH (SEQ ID NO:23)

Figure 3

```
                                              1                                                                          80
ZM-MIOX EST EL01N0202D10.b (W22) (SEQ ID NO:24)  (1) --------------------------------------------------------------------------------
Maize MIOX (B73) (SEQ ID NO:2)                   (1) MTITIEQPQLDAVAERKVPGGGDPAELVLDAGFVVPDANAFGNTFRDYDAESERKQTVEEFYRVNHVRQTHEFVARMRAE
Consensus (SEQ ID NO:25)                         (1)

81                                                                         160
ZM-MIOX EST EL01N0202D10.b (W22)                (1) -----------------NEFIDDSDPDLDMPQIEHLLQTAEAIRKDYPDEDWLHITGLIHDLGKVLLHPSFGELPQWAY
Maize MIOX (B73)                                (81) YGRLDKTEMGIWECIELLNEFIDDSDPDLDMPQIEHLLQTAEAIRKDYPDEDWLHITGLIHDLGKVLLHPSFGELPQWAY
Consensus                                       (81)              NEFIDDSDPDLDMPQIEHLLQTAEAIRKDYPDEDWLHITGLIHDLGKVLLHPSFGELPQWAV 161                                                                        240
ZM-MIOX EST EL01N0202D10.b (W22)                (63) VGDTFPVGCAYDECNVHFKYFKENPDYHNPKLNTKLGVYSEGCGLDKVLMSWGHDDYMYLVAKENKCTLPSAGLFIIRYH
Maize MIOX (B73)                                (161) VGDTFPVGCAYDECNVHFKYFKENPDYHNPKLNTKLGFTSEGCCNVYLMSWGHDDYMYLVAKENKCTLPSSAGLFIIRYH
Consensus                                       (161) VGDTFPVGCAYDECNVHFKYFKENPDYHNPKLNTKLGVYSEGCGLXKVLMSWGHDDYMYLVAKENKCTLPSAGLFIIRYH 241                                                         306
ZM-MIOX EST EL01N0202D10.b (W22)                (143) SKYPLHKHGAYTHLMDDEDKENLKWLHVFNKYDLYSKSNSRIDVEEVKPYMSLIDKYFPAKLRW-
Maize MIOX (73)                                 (241) SFYPLHKHGAYTHLMDDEDKENLKWLHVFNKYDIYSTSNSRIDVEEVKPYMSLIDKYFAKLRW-
Consensus                                       (241) SFYPLHKHGAYTHLMDDEDKENLKWLHVFNKYDLYSKSNSRIDVEEVKPYMSLIDKYFPAKLRW
```

Figure 4-2

5' UTR (2 total)

MI1PS3 5UTR
    Start: 1707   End: 1846

MI1PS3 5UTR
    Start: 2892   End: 3031 (Complementary)

RNA - Misc. (4 total)

MI1PS3 (TR2)
    Start: 1847   End: 2489

MI1PS3 (TR3)
    Start: 2499   End: 2890 (Complementary)

ZM-MIOX (TR1)
    Start: 4156   End: 4776 (Complementary)

ZM-MIOX (TR2)
    Start: 4791   End: 5130

```
   1  AACACTGATA GTTTAAACTG AAGGCGGGAA ACGACAAATCT GATCATGAGC GGAGAATTAA GGGAGTCACG TTATGACCCC CGCCGATGAC GCGGGACAAG
 101  CCGTTTTACG TTTGGAACTG ACAGAACCGC AACGTTGAAG GAGCCACTCA GCAAGCTGGT ACGATTGTAA TACGACTCAC TATAGGGCGA ATTGAGCGCT
 201  GTTAAACCGC TCTTCAACTG GAAGAGCGGT TACCCGGACC GGAATTCGAG TCGACGGTAT CGATAAGCTT GCCGAGTGCC ATCCTTGGAC ACTCGATAAA
 301  GTATATTTTA TTTTTTTTAT TTTGCCAACC AAACTTTTTG TGGTATGTTC CTACACTATG TAGAATCTACA TGTACCATTT TGGCACAATT ACATATTTAC
 401  AAAAATGTTT TCTATAAATA TTAGATTTAG TTCGTTTATT TGAATTTCTT CGGAAAATTC ACATTTAAAC TGCAAGTCAC TCGAAACATG GAAAACCGTG
 501  CATGCAAAAT AATGATATG AGCACAAGTT ACGACCGATT ACGAAGCAG TCAGAAGCAG GAAATTAATG AAACTTGTCC ACATGTCATG TGCTCACTAA ACATGACCGT
 601  GAACTTGTTA TCTAGTTGTT TAAAAATTGT ATAAAACACA AATAAAGTCA TATGTGTAGA TGTGACGTAC AAACTTAAGTG ACATGTCATG ATATCATATA TAGAGGTTGT
 701  GATAAAAATT TGATAATGTT TCGGTAAAGT TCCGATAAAA AGTACTCGAC AAAGAAGCCG TTGTCGATGT ACCTACACAT AAAATCATAG AGTTTCAATG TAGTTCACTC
 801  GACAAAGACT TTGTCAAGTG TCCAGATAAA TTCAGGCTTT GACACTCGGC AAAGCGCTCG ATTCCAGTAG ACTGTTCGTC GAGATCTCTT TGTCGAGTGT CACACTAGGC
 901  AAGTCTTTA CGGAGTGTTT TTCAGGCTTT TAAAGTTTAG CTTCCTGCTA AACTTTAGCT ATATGAATTG AAGTGCTAAA TGACAGTAAT TTGCATCAAA AATAGCTAGG AGATTTAGGC
1001  CCCGTTTCAA TCTCACGGGA TAAAGTTTAG CTTCCTGCTA AACTTTAGCT ATATGAATTG AAGTGCTAAA GTTTAGTTTC AATTACCACC ATTAGCTCTC
```

Figure 4-3

```
1101  CTGTTTAGAT  TACAAATGGC  TAAAAGTAGC  TAAAAAATAG  CTGCTAAAGT  TTATCTCGCG  AGATTGAAAC  AGGGCCTTAA  AATGAGTCAA  CTAATAGACC
1201  AACTAATTAT  TAGCTATTAG  TCGTTAGCTT  CTTTAATCTA  AGCTAAAACC  AACTAATAGC  TTATTTGTTG  AATTACAATT  AGCCAACGG   AATTCTCTGT
1301  TTTTCTAAAA  AAAAACTGCC  CCTCTCTTAC  AGCAAATTGT  CCGCTGCCCG  TGTTCCAGAT  ACAATGAACG  TACCTAGTAG  GAACTCTTTT  ACACGCTCGG
1401  TCGCTCGCCG  CGGATCGGAG  TCCCCGGAAC  ACGACACCAC  TGTGGAACAA  GACAAAGTCT  GCTCAGAGGC  GGCCACACCC  TGGGCTGCAC  CGAGCCGGAG
1501  CCCGGATAAG  CACGGTAAGG  AGAGTACGGC  GGGACGTGGC  GACCCGTTGC  TCTGCTGCCA  CGCAGCCTTC  CTCCACGTAG  CCCGGCGGCC  GGCCACGTA
1601  CCAGGGCCCG  GCGCTGGTAT  AAATGCGCGC  CACCTCCGCT  TTAGTTCTGC  ATACAGCCAA  CCCAAGGATC  CAACACACAC  CCGAGGATAT  CACAGTCGAG
1701  GGTCGACCCA  CGCGTCCGGC  CCAACAAAGG  AGCGCGGCGG  CCCCTCCTTC  CTTCCTCCCA  CTTCTCTCGC  GCCGCGCTCG  CTTACCTCGC  CTCGCATTCC
1801  GTTCGAGCAG  GGGAGCGGCA  GTGAGAAGGG  AGGGAATTAA  GGCAAGATGT  TCATCGAGAG  CTTCCGCGTC  GAGAGCCCCC  ACGTGCGGTA  CGGCCCGACG
1901  GAGATCGAGT  CGGAGTACCG  GTACGACACG  ACGGAGCTGG  TCGTTGTGGG  TGGGAGGCA   GCCTCCCGCT  GGTCGTCCG   CCCAAGTCC   GTCAAGTACA
2001  ACTTCCGGAC  CAGCACCGG   GTCCCAAGAC  TCGGGGTCAT  GCTGTTGAGG  TGGGAGGCA   ACAACGGTCG  CACCGGTGACG GCTGGGGTCA  TTGCCAACAG
2101  GGAGGGGATC  TCATGGGCGA  CCAAGGACAA  GGTGCAGCAA  GCCAACTACT  ACGGCTCCCT  CACCCAGGCT  TCCACCATCA  GAGTAGGCAG  CTACACGGG
2201  GAGGAGATAT  ATGCGCCGTT  CAAGAGCCTC  CTGGACATTG  TGAACCCAGA  CGACCTTGTG  TTTGGAGGCT  GGGACATCAG  CAGCATGAAC  CTGGCAGATG
2301  CCATGACCAG  GGCCAAGGTG  CTGACATTG   CTCGTGCCAA  GCAGCTCAGG  CCCTACATGG  AGTCCATGGT  GCCACTTCCC  GGTGTCTATG  ATCCGACTT
2401  CATCGCCGCT  AACCAGGGCT  CTCGTGCCAA  GGCGCATATA  TCTCCTCCCC  GTTGTAGCTG  CCCTACTCTGA TGGTGGAAGC  ATGATCCAAT  CTAGAAACCA
2501  TGGGTAGGAG  GCTCTTGAAC  TCCTTGGTCG  CCCATGAGAT  TTGGCAATGA  CCCCAGCCGT  CACCGTGGAC  CTGGGTGAGG  GAGCCGTAGT  AGTTGGCTTG
2601  CTGCACCTTG  TGGGACCGG   GGTGCTGGTC  TACTCCGGTC  ACTTGACGGA  CCCAGCCAG   CAGGCGCGCC  CGGTTGTTGC  GTCCTTGGCC  CACAACATG
2701  ACCCCGAGCT  GCTCGTCGT   TGGGACCGG   TACTCCGGTC  CGGAAGTTGT  ACTTGACGGA  CGCACCCAGC  GGAGGCGCC   GTCCTTGGCC  CACAACATG
2801  GCTCCGTCGT  GTCGTACCGG  TACTCCGGTC  CGATCTCGTC  CGGAAGTTGT  ACTTGACGGA  GGCTCTGTCA  TGCTGTAGTT  CTTCACCAA   TCTTGCTTA
2901  ATTCCCTCCC  TTCTCACTGC  CGCTCCCCTG  CTCGAACGGA  ATGCGAGGCG  AGTAAGCGA   GCGCCGCGCG  AGAGAAGTGG  GAGGAAGGAA  GGAGGGCCG
3001  CCGCGCTCCT  TTGTTGGGGC  GGACGCGTGG  GTCGACCTGC  AGAAGCTTCG  GTCCGGGTCA  CCTTTGTCCA  CCAAGATGGA  ACTGCGCCG   CTCATTAATT
3101  AAGTCAGGCG  CGCCTCTAGT  TGAAGACACG  TTCATGTCTT  CATCGTAAGA  AGACACTCAG  TAGTCTTCGG  CGAATTCGAG  CGAATTCGAG  GATCCGATTG
3201  ACTATCTCAT  TCCTCCAAAC  CCAAACACCT  CAAATATATC  TGCTATCGGG  ATTGGCATTC  CTGTATCCCT  ACGCCCGTGT  ACCCCTGTT   TAGAGAACCT
3301  CCCAAGGTAT  AAGATGGCGA  AGATTATTGT  TGTCTTGTCT  TTCATCATAT  ATCGAGTCTT  TCCCTAGGAT  ATTATTATTG  GCAATGAGCA  TTACACGGTT
3401  AATGATTGA   GAGAACATGC  ATCTCACCTT  CAGCAAATAA  TTACGATAAT  CCATATTTTA  CGCTTCGTAA  CTTTCCATGA  GTTTCGATAT  ACAAATTGT
3501  TTTCTGGACA  CCCTACCATT  CATCCTCTTC  GGAGAAGAGA  CGAAGTGTCC  TCAATTTAAA  TATGTTGTCA  TGCTGTAGTT  CTTCACCAAT  TCTCAACAGG
3601  TACCAAGCAC  ATTGTTTCCA  CAAATTATAT  TTTAGTCACA  ATAAATCTAT  ATTATTATTA  ACGGAAGACA  AAAGAAGTAA  ACTATACTAG  CGTCAGATG   CTTTTACTAG
3701  TTCTTGCTAG  TATGTGATGT  AGTCTACGT   GGACCAGAAA  ATAGTGAGAC  ACGGAAGACA  AAAGAAGTAA  ACCTCGTATA  AAGAGGCCCG  GACTACGGCC  CACATGAGAT
3801  TCGGCCCCGC  CACCTCCGGC  AACCAGCGGC  CGATCCAACG  CCCCCGACAC  GAAGTGCGCG  CACACACACA  ACCTCGTATA  TATCGCCGCG  CGGAAGCGGC  GGACCCAGG
3901  AAGCCTTGTC  CTCGACACCC  CCTACACAG   TGTCGGCCTG  CCTCGCCCTC  ATCTACCTCA  CTCGTAGTCG  TGCGTCCCAC  GCGCCCGCG   CAGATCCCGC  CTCCGCCGT
4001  TGCCACGCCC  TCTATAAACA  CCCAGCTCTC  AATGGAAGG   CCATGGAAAG  TACCAAGATG  GCCGCGGAAG  GAAGGGTGCA  TTCGATATCG  GATCATGGA   GATCTGTCGA
4101  CTCTAGACCC  GGGTGGATCC  AATCTAGAAA  TGACACCTT   GTTGAGGCCG  CCGCCTCCG   AGTAGACCCG  CAACTTGGTG  CTTGTTCTCC  TTGGCCACCA  GGTACATGTA
4201  GTCGTCGTGG  CCCATGACA   TGACACCTT   GACGTTGCAC  TGTCTGTATG  GCCGCCGCAG  CTGCCCTCCG  AGTAGACCCG  GGTTGTTGTA  GTCGGGGTTC  GTCGGGGTTC
4301  TCCTTGAAGT  ACTTGAAGTG  GACGTTGCAC  AGTCGTCGAC  TGTCTGTATG  CGCAGCCTCCG GAGGTCGAGC  CAGCCACCACTG  GCCTCGGCCG  TCTGCAGCTTG
4401  GGTGCAGCAG  CACCTTGCCC  AGTCGTCGAC  TGAGTCCGAC  GTCAGTGGAG  CAGTCAGTGG  CGGGGTAGTC  CTCACCAGCAG GCCTCGGCCG  TCTGCAGCTTG
4501  GTGCTCGATC  TGGGGCATGT  CCGCCCGCAT  CCGCGCCACG  AACTCGTGCG  TCTGCCTCAC  GTGTTCAGCAG  CTCGATGAACT  CCTCTACGT   GCCTCGGCCG  CCATCTCCGT  CTTGTCCAGC
4601  CGTCCGTACT  CGCCGAAGTA  TTGCCGAAGG  CGTTGGCGTC  CGGCACGACG  TCTGCCTCAC  CCCGCGGAC   CTCCGCGGAC  CGAATTCGAG  CTGCAGCCG   TCCGACTCCG
4701  CGTCGTAGTC  CCTGAAGTTA  TTGCCGAAGG  ATGCGGGCGG  AGTACGGACAA ACGGAGATGG  GCATCTGGGA  GTGCATCGAG  CGAATTCGAG  GTGAGGCAGA
4801  CGCACGAGTT  CGTGGCCGCG  CCGGACCTGG  ACATGCCCCA  GATCGAGCAC  CTGCTCGACC  CAAGCTTCAGG GCATCTGGGA  GTCATCCGAG  CTGCATCATCG AGTTCATCGA
4901  CGACAGCGAC  CCGGACCTGG  ACATGCCCCA  GGGCAAGGTG  CTGCTCGACC  CAAGCTTCAGG GAAGCTCCCT  CAGTGGGCTG  CACCTTCCCC  GCTCCACCTC
5001  ACCGACTCA   TCCACGACCT  GGGCAAGGTG  ACATGCCCCA  CTGCTCGACC  CAAGCTTCAGG GGAGCTCCCT  CAGTCGGTGA  CACCTTCCCC  GCTCCACCTC  GTCGGCTGCG
5101  CATACGACGA  GTCAACGTC   CACTTCAAGT  GGGCAAGGTG  CTCGAGCCCA  CAAGCTTCAGG AAAGATCTAA  GCATGCAAGG  GCCCCGGCCG  AAGCTTGGCC  TAGAAGCCA
```

Figure 4-4

```
5201 TTTAAATCCT GAGGATCTGG TCTTCCTAAG GACCCGGGCG GTCCGATTAA ACTTTAATTC GGACCGAAGC TTCTGCAGGA ATTCCTGCAG TGCAGCCGTGA
5301 CCCGGTCGTG CCCCTCTCTA GTGGATCTGA GCTTCTAGAA ATAC
```

Figure 5-2

```
   1  GACCGGAATT CGAGCTCGGT ACCCAGCTTA GCTAGATCAT TTGTAAGAAT GCAACTTGTT
  61  CATATAGCAT GGCTACAGCC TACATCATCT GAAATAGACC TGTTTATAGG ATACCTAAGC
 121  TCAATTCACC CTATATCTAA AACCTACGAG GCCTAAACAC ACCCGTCCTC AAGAAAACGA
 181  CCAGACCAAA CCAAACCATG CGTCCGCGTC ATGGTTTTGT AGACACGTTT ACGTATCAAT
 241  TATAGTGTTC TGATTTTTAT ATTCTCCTAA TTATTTAGAG CTAAATTTAT TTTTATGATA
 301  GCAGAGATCT AAATATTTTT GTTTTGATTT TTTATATACT AAAATCATCT CTACAATATT
 361  AGAGATTTTA AATGCTCAGA AGAATTTTAC TTGAATTAAA ACCTTTACTG ATTTTTAACT
 421  AAAACGGAGA TCAAAAGAAA TCTATCCAAG GCTGCCTCTA AGAGCCTTCG TGTCTCGTTT
 481  TCTTATTTCA GACTTCACTC ATCTTCTTAT TTCAGGCTCC ACTATATAAG GTGGTCTCTA
 541  GTATCTTTCC TATCACATAT CCTATTTAAA ACTTTAGTAT ATAAAACATT ATAATTCATA
 601  ATATAAATCG ATTATTTTAC ACGATCTCAG CCTAAAAGCG GTAATATGCA CGCTCTGAGC
 661  ATGGCCCAAG CTCCACGTTA ACCGTTCTGT CAAAAAAAAA AACATCTAGT CTAGAATGGA
 721  AAACACACGA TTTTAGAAGT TAGGACTAGT TTGGCAACTC AATTTTCCAA ATGATTCTCA
 781  TTCTTTTAAG AGGATTAAT TTATTTTTG GTAAAATAGG AATCACTAGA AACTCTATTT
 841  TTTCAAGAGA AGTAAGCTA TTTTTTTAGA AAAATAAAAA ATCCCTTAAA AAATATTGTT
 901  CGTAAATTAG CCCTAAGATG GACTAAAAAT CTGTTTTAT AGAATAGGGA GGGATCGAGC
 961  AACCGCCAAA TCTACGCGCC AAAAAGGTAC CTTTTCCGTG AATAAACACG ACTGCGGCGA
1021  TNACGATCTG ATCGGAGCAG GTAGAATAAA ATGGAGCAGC GGAATAGTGT GGGAAGCACA
1081  AGCACCAGGA GGAGCTGAAA CCGTCCACTC CGCGCCAACA GATCCCCACT CCGGCCGGCA
1141  CCCGAGTGTG CGAGACGTGT GGGGCTGATC TGACGAGCCT GGAAGAAGAA GAAGAAAAAA
1201  AAGTCCTCAC GCTCCTGCTT GGCTCCATCG ACAGCTCACT AGCTGTTACC GGATGCTCGC
1261  GTCTCTGGTG CCTCTCGATT CATCATCCAT CGTTGGTGGC GCCGGCGGGG CGGCAAAGGT
1321  TCTGATTCCG CAGCAGCCAA GTGCTCCTCC TGCAGACGAA AATGACGGCA GAGGTTGGCG
1381  TTGATCCAGG AGACTCATCA GTTTAGTTTA ATAATGAATC TGTAGCAGGC GCTTCAGTCT
1441  CTCATCGGAT GAGCGAGCAG CTTAGCAGAG CAGGTGGTGG TCCCTGGCTC GCCCACGTCC
1501  ATTCTTTCCC GCCCGTCCTG CCGTCCACTC CGCGCCACTC TTATACCCCT CCTCGCCCAC
1561  CCTGCCATCC TCACCATCGC AATTCACAAG CAAAGCAATC AGAGCCAAGC ACCCACGTC
1621  CTCCTTTCTT TCCTTCGACT CATCAAAGCC GGGATCCATG ACGATCACCA TTGAACAGCC
1681  CCAGCTCGAT GCGGTGGCGG AGAGGAAAGT CCCCGGCGGA GGTGACCCCG CGGAGCTGGT
1741  GCTCGACGCC GGCTTCGTCG TGCCGGACGC CAACGCCTTC GGCAATACCT TCAGGGACTA
1801  CGACGCGGAG TCGGAGCGGA AGCAGACGGT AGAGGAGTTC TACGGGTGA ACCACGTGAG
1861  GCAGACGCAC GAGTTCGTGG CGCGGATGCG GGCGGAGTAC GGCGGCTGG ACAAGACGGA
1921  GATGGGCATC TGGGAGTGCA TCGAGCTGCT GAACGAGTTC ATCGACGACA GCGACCCGGA
1981  CCTGGACATG CCCCAGATCG AGCACCTGCT GCAGACCGCC GAGGCCATCC GCAAGGACTA
2041  CCCCGACGAG GACTGGCTCC ACCTCACCGG ACTCATCCAC GACCTGGGCA AGTGCTGCT
2101  GCACCCAAGC TTCGGGGAGC TCCCTCAGTG GGCTGTCGTC GGTGACACCT TCCCGTCGG
2161  CTGCGCATAC GACGAGTGCA ACGTCCACTT CAAGTACTTC AAGGAGAACC CGACTACCA
```

Figure 5-3

```
2221 CAACCCGAAG CTCAACACCA AGTTGGGGT CTACTCGGAG GGCTGCGCC TCAACAAGGT
2281 GCTCATGTCA TGGGGCCACG ACGACTACAT GTACCTGGTG GCCAAGGAGA ACAAGTGCAC
2341 CCTTCCTTCC GCGGGCTGT TCATCATCAG ATACCACTCG TTCTACCCC TGCACAAGCA
2401 TGGAGCCTAC ACACACCTGA TGGACGATGA GGACAAGGAG AACCTCAAGT GGCTGCATGT
2461 GTTCAACAAG TATGACCTGT ACAGCAAGAG CAACAGCAGG ATCGACGTGG AGGAGGTGAA
2521 GCCCTACTAC ATGTCCCTAA TCGACAAGTA CTTCCCGGCC AAGCTAAGAT GGTGACCCAT
2581 CTGCAGTCGA CGTGCAAAGG TCCGCCTTGT TTCTCCTCTG TCTCTTGATC TGACTAATCT
2641 TGGTTTATGA TTCGTTGAGT AATTTTGGGG AAAGCTTCGT CCACAGTTTT TTTTCGATGA
2701 ACAGTGCCGC AGTGGCGCTG ATCTTGTATG CTATCCTGCA ATCGTGGTGA ACTTATTTCT
2761 TTTATATCCT TTACTCCCAT GAAAAGGCTA GTAATCTTTC TCGATGTAAC ATCGTCCAGC
2821 ACTGCTATTA CCGTGTGGTC CATCCGACAG TCTGGCTGAA CACATCATAC GATCTATGGA
2881 GCAAAAATCT ATCTTCCCTG TTCTTTAATG AAGGACGTCA TTTTCATTAG TATGATCTAG
2941 GAATGTTGCA ACTTGCAAGG AGGCGTTTCT TTCTTTGAAT TTAACTAACT CGTTGAGTGG
3001 CCCTGTTTCT CGGACGTAAG GCCTTTGCTG CTCCACACAT GTCCATTCGA ATTTTACCGT
3061 GTTTAGCAAG GGCGAAAAGT TTGCATCTTG ATGATTAGC TTGACTATGC GATTGCTTTC
3121 CTGGACCCGT GCAGCTGGAT CCCGGGTCAC CATCTTAGCT TGGCCGGGAA GTACTTGTCG
3181 ATTAGGGACA TGTAGTAGGG CTTCACCTCC TCCACGTCGA TCCTGCTGTT GCTCTTGCTG
3241 TACAGTCAT ACTTGTTGAA CACATGCAGC CACTTGAGGT TCTCCTTGTC CTCATCGTCC
3301 ATCAGGTGTG TGTAGGCTCC ATGCTTGTGC AGGGGGTAGA ACGAGTGGTA TCTGATGATG
3361 AACAGCCCCG CGGAAGGAAG GGTGCACTTG TTCTCCTTGG CCACCAGGTA CATGTAGTCG
3421 TCGTGGCCCC ATGACATGAG CACCTTGTTG AGGCCGCAGC CCTCCGAGTA GACCCCAAC
3481 TTGGTGTTGA GCTTCGGGTT GTGGTAGTCG GGGTTCTCCT GAAGTACTT GAAGTGGACG
3541 TTGCACTCGT CGTATGCGCA GCCGACGGGG AAGGTGTCAC CGAGCAGAGC CCACTGAGGG
3601 AGCTCCCCGA AGCTTGGGTG CAGCAGCACC TTGCCCAGGT CGTGGATGAG TCCGGTGAGG
3661 TGGAGCCAGT CCTCGTCGGG GTAGTCCTTG CGGATGGCCT CGGCGGTCTG CAGCAGGTGC
3721 TCGATCTGGG GCATGTCCAG GTCCGGGTCG CTGTCGTCGA TGAACTCGTT CAGCAGCTCG
3781 ATGCACTCCC AGATGCCCAT CTCCGTCTTG TCCAGCCGCC CGTACTCCGC CCGCATCCGC
3841 GCCACGAACT CGTGCGTCTG CCTCACGTGG TTCACCCGGT AGAACTCCTC TACCGTCTGC
3901 TTCCGCTCCG ACTCCGCGTC GTAGTCCCTG AAGGTATTGC CGAAGGCGTT GGCGTCCGGC
3961 ACGACGAAGC CGGCGTCGAG CACCAGCTCC GCGGGGTCAC CTCCGCCGGG GACTTTCCTC
4021 TCCGCCACCG CATCGAGCTG GGGCTGTTCA ATGGTGATCG TCATGGATCC AAGCTTGGTC
4081 ACCCGGTCCG GGCCTAGAAG GCCGATCTCC CGGGC
```

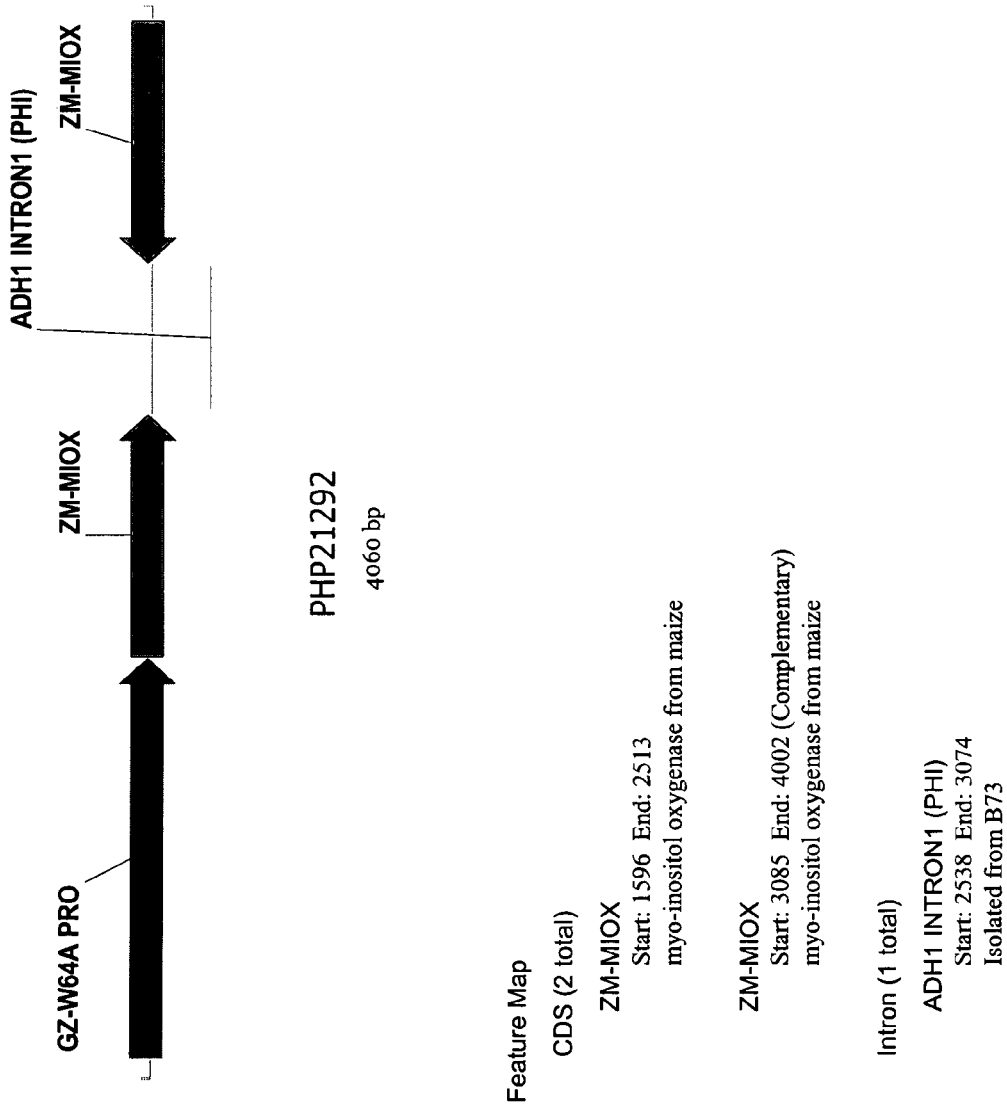

Figure 6-2

Promoter Eukaryotic (1 total)

GZ-W64A PRO
Start: 74   End: 1590
Maize 27 KD Gamma zein promoter, isolated from W64A line

```
   1 TCCGGCCAGA ATGGCCCGGA CCGGGTTACC CGGTCCGGAA TTCGAGCTCC ACCGCGGTGG
  61 CGGCCGCTCT AGATTATATA ATTTATAAGC TGAAACAACC CGGCCCTAAA GCACTATCGT
 121 ATCACCTATC TGAAATAAGT CACGGGTTTC GAACGTCCAC TTGCGTCGCA CGGAATTGCA
 181 TGTTTCTTGT TGGAAGCATA TTCCAGCATA CTCCACACAT AAAGGTTTAT GTATAAACTT
 241 ACATTTAGCT CAGTTTAATT ACAGTCTTAT TTGGATGCAT ATGTATGGTT CTCAATCCAT
 301 ATAAGTTAGA GTAAAAAATA AGTTTAAATT TTATCTTAAT TCACTCCAAC ATATATGGAT
 361 TGAGTACAAT ACTCATGTGC ATCCAAACAA ACTACTTATA TTGAGGTGAA TTTGGATAGA
 421 AATTAAACTA ACTTACACAC TAAGCCAATC TTTACTATAT TAAAGCACCA GTTTCAACGA
 481 TCGTCCCGCG TCAATATTAT TAAAAACTC CTACATTTCT TTATAATCAA CCCGCACTCT
 541 TATAATCTCT TCTCTACTAC TATAATAAGA GAGTTTATGT ACAAAATAAG GTGAAATTAT
 601 GTATAAGTGT TCTGGATATT GGTTGTTGGC TCCATATTCA CACAACCTAA TCAATAGAAA
 661 ACATATGTTT TATTAAAACA AAATTTATCA TATATCATAT ATATATATAT ACATATATAT
 721 ATATAAACCG TAGCAATGCA CGGGCATATA ACTAGTGCAA CTTAATACAT GTGTGTATTA
 781 AGATGAATAA GAGGGTATCC AAATAAAAAA CTTGTTCGCT TACGTCTGGA TCGAAAGGGG
 841 TTGGAAACGA TTAAATCTCT TCCTAGTCAA AATTGAATAG AAGGAGATTT AATCTCTCCC
 901 AATCCCCTTC GATCATCCAG GTGCAACCGT ATAAGTCCTA AAGTGGTGAG GAACACGAAA
 961 CAACCATGCA TTGGCATGTA AAGCTCCAAG AATTTGTTGT ATCCTTAACA ACTCACAGAA
1021 CATCAACCAA AATTGCACGT CAAGGGTATT GGGTAAGAAA CAATCAAACA AATCCTCTCT
1081 GTGTGCAAAG AAACACGGTG AGTCATGCCG AGATCATACT CATCTGATAT ACATGCTTAC
1141 AGCTCACAAG ACATTACAAA CAACTCATAT TGCATTACAA AGATCGTTTC ATGAAAAATA
1201 AAATAGGCCG GACAGGACAA AAATCCTTGA CGTGTAAAGT AAATTTACAA CAAAAAAAAA
1261 GCCATATGTC AAGCTAAATC TAATTCGTTT TACGTAGATC AACAACCTGT AGAAGGCAAC
1321 AAAACTGAGC CACGCAGAAG TACAGAATGA TTCCAGATGA ACCATCGACG TGCTACGTAA
1381 AGAGAGTGAC GAGTCATATA CATTTGGCAA GAAACCATGA AGCTGCCTAC AGCCGTCTCG
1441 GTGGCATAAG AACACAGAA ATTGTGTTAA TAATCAAAG CTATAAATAA CGCTCGCATG
1501 CCTGTGCACT TCTCCATCAC CACCACTGGG TCTTCAGACC ATTAGCTTTA TCTACTCCAG
1561 AGCGCAGAAG AACCCGATCG ACAGATATCG GATCCATGAC GATCACCATT GAACAGCCCC
1621 AGCTCGATGC GGTGGCGGAG AGGAAAGTCC CCGGCGGAGG TGACCCCGCG GAGCTGGTGC
1681 TCGACGCCGG CTTCGTCGTG CCGGACGCCA ACGCCTTCGG CAATACCTTC AGGGACTACG
1741 ACGCGGAGTC GGAGCGGAAG CAGAGCGTAG AGGAGTTCTA CGGGTGCAAC CACGTGAGGC
1801 AGACGCACGA GTTCGTGGCG CGGAGTACGG CGGAGTACGG GCGGCTGGAC AAGACGGAGA
```

Figure 6-3

```
1861  TGGGCATCTG GGAGTGCATC GAGCTGCTGA ACGAGTTCAT CGACGACAGC GACCCGGACC
1921  TGGACATGCC CCAGATCGAG CACCTGCTGC AGACCGCCGA GGCCATCCCG AAGGACTACC
1981  CCGACGAGGA CTGGCTCCAC CTCACCGGAC TCATCCACGA CCTGGGCAAG GTGCTGCTGC
2041  ACCCAAGCTT CGGGGAGCTC CCTCAGTGGG CTGTCGTCGG TGACACCTTC CCCGTCGGCT
2101  GCGCATACGA CGAGTGCAAC GTCCACTTCA AGTACTTCAA GGAGAACCCC GACTACCACA
2161  ACCCGAAGCT CAACACCAAG TTGGGGGTCT ACTCGGAGGG CTGCGGCCTC AACAAGGTGC
2221  TCATGTCATG GGGCCACGAC GACTACATGT ACCTGGTGGC CAAGGAGAAC AAGTGCACCC
2281  TTCCTTCCGC GGGGCTGTTC ATCATCAGAT ACCACTCGTT CTACCCCCTG CACAAGCATG
2341  GAGCCTACAC ACACCTGATG GACGATGAGG ACAAGGAGAA ACAGCAGGAT CCTCAAGTGG CTGCATGTGT
2401  TCAACAAGTA TGACCTGTAC AGCAAGAGCA ACAGCAGGAT CGACGTGGAG GAGGTGAAGC
2461  CCTACTACAT GTCCCTAATC GACAAGTACT TCCCGGCCAA GCTAAGATGG TGACCCATCT
2521  GCAGTCGACG TGCAAAGGTC CGCCTTGTTT CTCCTCGTCC TCTTGATCTG ACTAATCTTG
2581  GTTTATGATT CGTTGAGTAA TTTTGGGGAA AGCTTCGTCC ATCCTGCAAT ACAGTTTTTT TTCGATGAAC
2641  AGTGCCGCAG TGGCGCTGAT CTTGTATGCT AATCTTTCTC CGTGGTGAAC TTATTTCTTT
2701  TATATCCTTT ACTCCCATGA AAAGGCTAGT TGGCTGAACA CATCATACGA CGTCCAGCAC
2761  TGCTATTACC GTGTGGTCCA TCCGACAGTC GGACGTCATT TTCATTAGTA TCTATGGAGC
2821  AAAATCTAT CTTCCCTGTT CTTTAATGAA CTTTGAATTT AACTAACTCG TGATCTAGGA
2881  ATGTTGCAAC TTGCAAGGAG GCGTTTCTTT CCACACATGT CCATTCGAAT TTTACCGTGT
2941  CTGTTTCTCG GACGTAAGGC CTTTGCTGCT GATTTAGCTT GACTATGCGA TTGCTTTCCT
3001  TTAGCAAGGG CGAAAAGTTT GCATCTTGAT CTTTAGCTTG GCCGGAAGT ACTTGTCGAT
3061  GGACCCGTGC AGCTGGATCC CGGGTCACCA TCTTAGCTTG CAGTCGATC GTCGTTGC TCTTGCTGTA
3121  TAGGGACATG TAGTAGGGCT TCACCTCCTC CACGTCAGCA CTTGAGGTTC TCCTTGTCCT CATCGTCCAT
3181  CAGGTCATAC TTGTTGAACA CATGCAGCCA CTTGAGGTTC TCCTTGTCCT CATCGTCCAT
3241  CAGGTGTGTG TAGGCTTCCA GCTTGTGCAG GGGTAGAAC GAGTGGTATC GAGTGATGAA
3301  CAGCCCCGCG GAAGGAAGGG TGCACTTGTT CTCCTTGGCC ACCAGGTACA TGTAGTCGTC
3361  GTGGCCCCAT GACATGAGCA CCTTGTTGAG GCCGCAGCCC TCCGAGTAGA CCCCAACTT
3421  GGTGTTGAGC TTCGGGTTGT GGTAGTCGGG GTTCTCCTTG AAGTACTTGA AGTGGACGTT
3481  GCACTCGTCG TATGCGCAGC CGACGGGGAA GGTGTCACCG ACGACAGCCC ACTGAGGGAG
3541  CTCCCCGAAG CTTGGGTGCA GCAGCACCTT GCCCAGGTCG TGGATGAGTC CGGTGAGGTG
3601  GAGCCAGTCC TCGTCGGGGT AGTCCTTGCG CGGGTCCTCG GATGGCCTCG GCGGTGTCGCA GCAGGTGCTC
3661  GATCTGGGGC ATGTCCAGGT CGGGTCGCT GTCGTCGATG AACTCGTTCA GCAGCTGAT
3721  GCACTCCCAG ATGCCCATCT TGCGTCTGCC CGTCTTGTC CAGCCGCCCG TACTCCGCCC GCATCCGCGC
3781  CACGAACTCG TGCGTCTGCC TCCGTCGCC TCACGTGGTT ACTCCCTGAA GGTATTGCCG AACTCCTCTA CCGTCTGCTT
3841  CCGCTCCGAC TCCGCGTCGT AGTCCCTGAA GGTATTGCCG AAGGCGTTGG CGTCCGGCAC
3901  GACGAAGCCG GCGTCGAGCA CCAGCTCCGC GGGGTCACCT GGTGATCGTC CGCCGGGGA CTTTCCTCTC
3961  CGCCACCGCA TCGAGCTGGG GCTGTTCAAT GGTGATCGTC CGCCGGGGA CTTTCCTCTC
4021  GGGTCACCCG GTCCGGGCCT AGAAGGCCGA TCTCCCGGGC
```

MODULATING *MYO*-INOSITOL CATABOLISM IN PLANTS

CROSS-REFERENCE PARAGRAPH

This application claims the benefit of U.S. Provisional Application No. 60/547,640, filed Feb. 25, 2004, which is herein incorporated by reference in its entirety.

FIELD OF THE INVENTION

The present invention relates generally to plant molecular biology. More specifically, it relates to nucleic acids and methods for modulating the expression in plants of myo-inositol oxygenase.

BACKGROUND OF THE INVENTION

Myo-inositol (MI) plays an important role in a variety of plant cellular processes with potentially significant agronomic impact. For example, MI is a precursor in the formation of the cell wall components hemicellulose and pectin, which affect plant processing properties and nutritional content. See, e.g., U.S. Pat. No. 6,194,638; U.S. Patent Application No. 20030079251; and Loewus and Murthy (2000) *Plant Sci.* 150:1-19, all of which are herein incorporated by reference. MI is also involved in the synthetic pathway leading to the production of phytic acid salts (phytates), which both reduce the nutritive content of feed and, in animal waste, are a major source of surface and ground water pollution. See, e.g., U.S. Pat. Nos. 6,197,561 and 6,291,224; and U.S. Patent Application No. 20030079247, all of which are herein incorporated by reference.

Catabolism of MI occurs via a single pathway, the MI oxidation pathway (see Loewus and Murthy (2000) *Plant Sci.* 150:1-19). The first committed step in this pathway is the conversion of MI to D-glucuronic acid (glucuronate) by the enzyme myo-inositol oxygenase (MIOX; synonymously meso-inositol oxygenase, myo-inositol:oxygen oxidoreductase, or EC 1.13.99.1). The MIOX protein has been isolated from a variety of organisms, including oat seedlings (Koller et al. (1976) *Mol. Cell. Biochem.* 10:33-39), and the corresponding gene sequence has been determined for, e.g., rats, mice, humans, and pigs. See Arner et al. (2001) *Biochem. J.* 360: 313-320, herein incorporated by reference.

In light of the involvement of MI in plant cellular processes, it would be advantageous to increase or decrease the amount of this compound in order to modulate these cellular processes, and thereby improve the agronomic properties of plants.

BRIEF SUMMARY OF THE INVENTION

Compositions and methods for modulating myo-inositol oxygenase (MIOX) expression and activity in a plant are provided. Compositions include nucleotide sequences for novel MIOX sequences obtained from maize, the amino acid sequences encoded by the nucleotide sequences of the invention, and variants and fragments thereof. Methods for modulating MIOX in a plant or plant part are also disclosed. The methods comprise introducing into a plant or a plant cell a nucleotide construct comprising a MIOX nucleotide sequence of the invention operably linked to a promoter that drives expression in a plant. The methods of the invention find use in, for example, modulating MIOX activity and MIOX content in a plant.

Transformed plants, plant parts, plant cells, and seeds, as well as methods for making such plants, plant parts, plant cells, and seeds are additionally provided.

BRIEF DESCRIPTION OF THE DRAWINGS

FIG. 3 shows MIOX variants obtained from different maize lines (i.e., allelic variants). ZM-MIOX EST EL01N0202D10.b, public EST (GenBank accession # CD447913; SEQ ID NO:24), was isolated from maize W22 library made from 7-23 DAP endosperm mRNA. Maize MIOX (B73) (SEQ ID NO:2) was isolated from maize line B73. A consensus sequence is provided in the figure and set forth in SEQ ID NO:25.

FIG. 6 shows a schematic representation of a MIOX expression cassette and a description of the features of the expression cassette. The sequence of SEQ ID NO:9 is further provided.

DETAILED DESCRIPTION OF THE INVENTION

Figure 2:
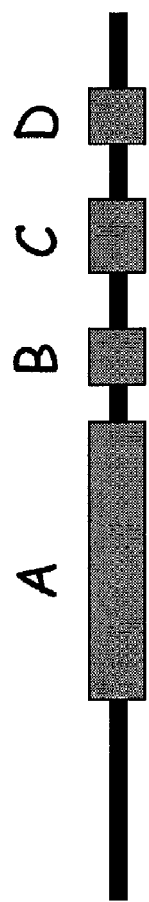
FIG. 2 shows conserved domains from MIOX amino acid sequences. See alignment in FIG. 1. The amino acid sequence for conserved domains A, B, C, and D are set forth in SEQ ID NOs:20, 21, 22, and 23, respectively. The function of the conserved domains is unknown.

Compositions and methods for modulating MIOX expression and/or activity within a plant or plant part are provided. Compositions of the invention include nucleic acid sequences for MIOX sequences and the amino acid sequences for the proteins or partial-length polypeptides encoded thereby. In particular, the present invention provides for isolated nucleic acid molecules comprising nucleotide sequences encoding the amino acid sequences shown in SEQ ID NO:2, and fragments and variants thereof. Further provided are polypeptides having an amino acid sequence encoded by a nucleic acid molecule described herein, for example, the sequence set forth in SEQ ID NO:1 and fragments and variants thereof.

Specifically, the present invention is directed to compositions comprising a novel corn MIOX nucleotide sequence, as given in SEQ ID NO:1; the MIOX amino acid sequence of SEQ ID NO:2, which is encoded by the nucleotide sequence of SEQ ID NO:1; derivatives and variants of these sequences; and, stably transformed plants and plant seed containing these sequences. These aspects of the invention are described in more detail elsewhere herein.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Optimally, an "isolated" nucleic acid is free of sequences (optimally protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed nucleotide sequences and proteins encoded thereby are also encompassed by the present invention. "Fragment" is intended to mean a portion of the nucleotide sequence or a portion of the amino acid sequence and hence protein encoded thereby. Fragments of a nucleotide sequence may encode protein fragments that retain the biological activity of the native protein and hence retain MIOX activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a MIOX nucleotide sequence that encodes a biologically active portion of a MIOX protein of the invention will encode at least 15, 25, 30, 35, 40, 45, 50, 55, 60, 65, 70, 75, 80, 85, 90, 95, 100, 125, 150, 175, 200, 225, 250, 275, or 300 contiguous amino acids, or up to the total number of amino acids present in a full-length MIOX protein of the invention (for example, 305 amino acids for SEQ ID NO:2). Fragments of a MIOX nucleotide sequence that are useful as hybridization probes or PCR primers generally need not encode a biologically active portion of a MIOX protein.

Figures 1, 4:
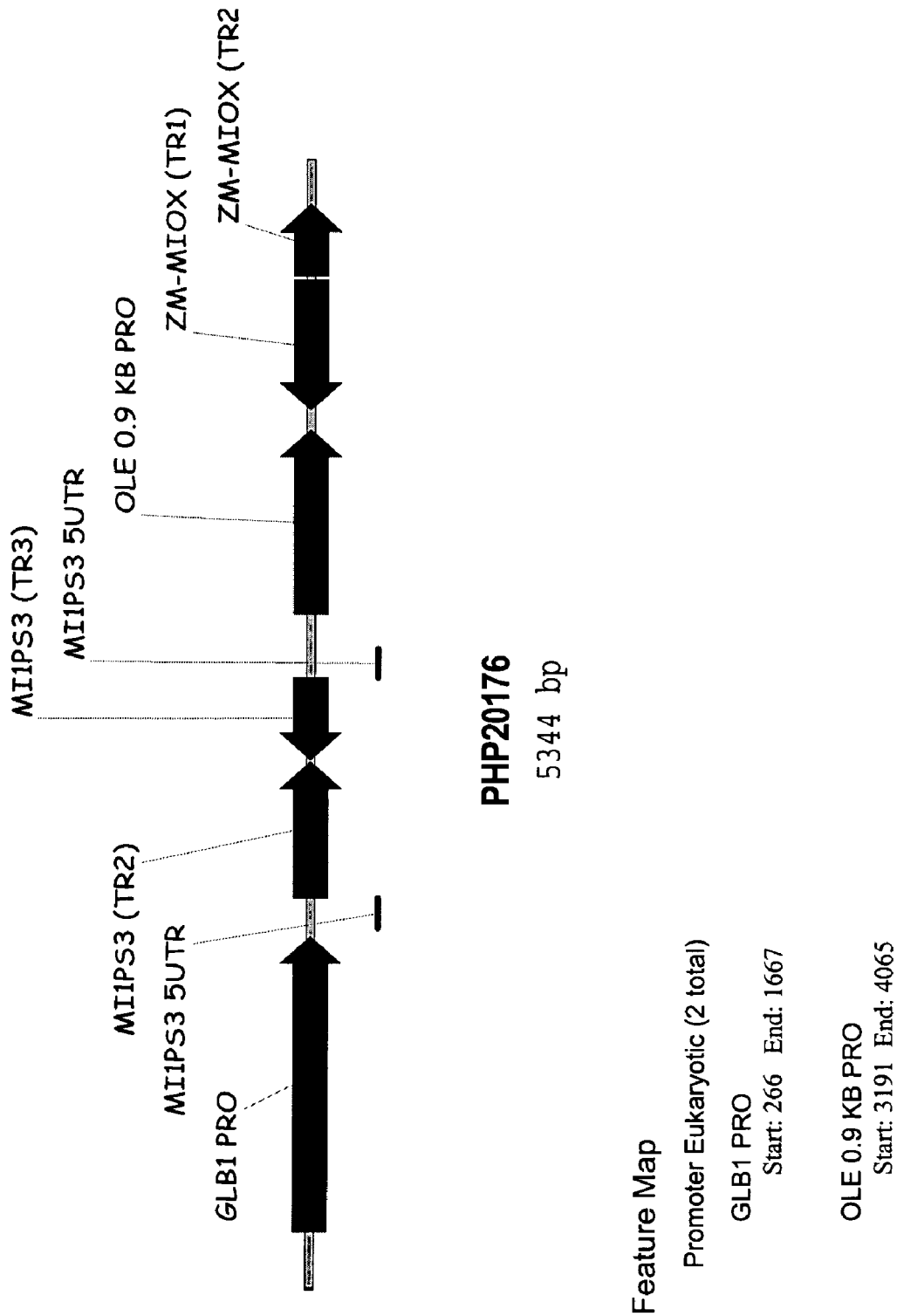
FIG. 1 shows an amino acid sequence alignment of the maize MIOX sequence (SEQ ID NO:2) of the present invention and MIOX sequences obtained from other species, including *Homo* MIOX AF197129, human MIOX (GenBank Accession # AF197129; SEQ ID NO:10); Pig MIOX AF401311, pig MIOX (GenBank Accession # AF401311; SEQ ID NO:11) Mus MIOX AF197127, mouse MIOX (GenBank Accession # AF197127; SEQ ID NO:12); *Rattus* MIOX AF197128, rat MIOX (GenBank Accession # AF197128; SEQ ID NO:13); *Drosophila* protein (GenBank Accession # NM_140299; SEQ ID NO:14); Pine MIOX, translated from *Pinus radiata* EST (GenBank accession # AA220903; SEQ ID NO:15); Soybean MIOX; (SEQ ID NO:16); *Arabidopsis* MIOX (GenBank Accession # NM_101319; SEQ ID NO:17); and Rice MIOX (SEQ ID NO:18). Amino acids conserved among species are shaded, and a consensus sequence is provided in SEQ ID NO:19.
FIG. 4 shows a schematic representation of a MIOX/MI1PS expression cassette and a description of the features of the expression cassette. The sequence of SEQ ID NO:7 is further provided.
Figures 1, 5:
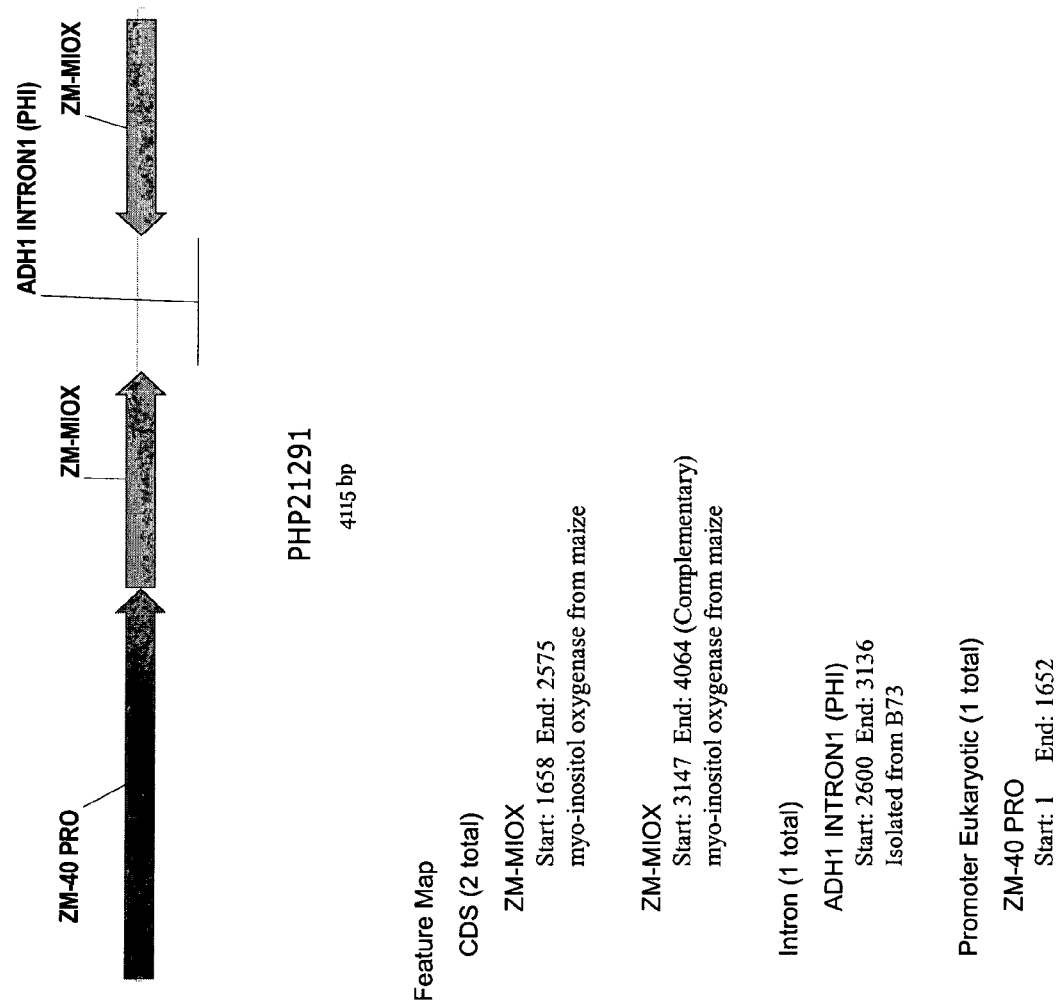
FIG. 5 shows a schematic representation of a MIOX expression cassette and a description of the features of the expression cassette. The sequence of SEQ ID NO:8 is further provided.
Figure 7:
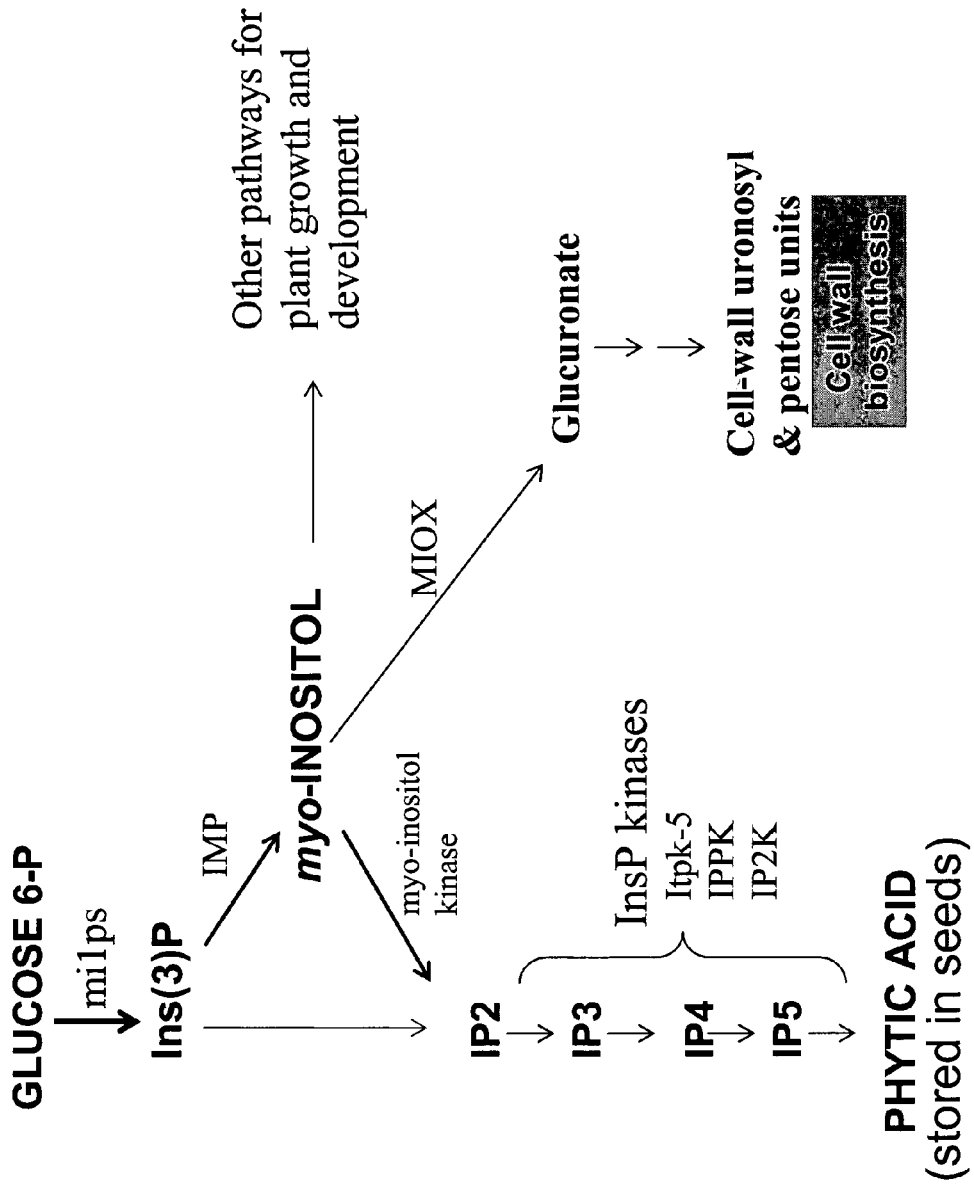
FIG. 7 provides a diagram of the biosynthesis and catabolism of myo-inositol. The pathways leading to phytic acid production in seeds and cell wall biosynthesis are also shown.

Thus, a fragment of a MIOX nucleotide sequence may encode a biologically active portion of a MIOX protein, or it may be a fragment that can be used as a hybridization probe or PCR primer using methods disclosed below. A biologically active portion of a MIOX protein can be prepared by isolating a portion of one of the MIOX nucleotide sequences of the invention, expressing the encoded portion of the MIOX protein (e.g., by recombinant expression in vitro), and assessing the activity of the encoded portion of the MIOX protein using any of the assays for measuring such activity described elsewhere herein, or using assays for such activity well-known to the skilled artisan. The choice of such fragments may be aided by in silico sequence comparisons between the MIOX sequences of the present invention and MIOX sequences from other species, e.g., using MIOX sequence comparisons such as that presented in Arner et al. (2001) *Biochem. J.* 360:313-320, and in FIG. 1. Such comparisons allow for the determination of the regions of the MIOX protein likely to preserve MIOX activity when present as fragments. Such comparisons also identify candidate regions for sequence modifications.

Thus nucleic acid molecules that are fragments of a MIOX nucleotide sequence comprise at least 16, 20, 50, 75, 100, 150, 200, 250, 300, 350, 400, 450, 500, 550, 600, 650, 700, 800, 900, 1,000, 1,100, or 1,200 contiguous nucleotides, or up to the number of nucleotides present in a full-length MIOX nucleotide sequence disclosed herein (for example, 1265 nucleotides for SEQ ID NO:1).

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the MIOX polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode a MIOX protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 2 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, MIOX activity as described herein. Such variants may result from, for example, genetic polymorphism or from human manipulation. Biologically active variants of a native MIOX protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the MIOX proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

In some embodiments, the selection of amino acids to alter is made by consulting the protein alignment of the MIOX sequence of the invention with MIOX sequences isolated from other species. See FIG. 1. An amino acid is selected for mutation that is deemed not to be under high selection pressure (i.e., not highly conserved) and that is rather easily substituted by an amino acid with similar chemical characteristics (i.e., similar functional side-chain). Using the protein alignment set forth in FIG. 1, an appropriate amino acid can be changed. In particular aspects of the invention, amino acid substitutions outside the conserved regions are made. It is recognized, however, that conservative substitutions can be made in the conserved regions in FIG. 1 without altering function. In addition, one of skill will understand that functional variants of the MIOX sequence of the invention can have minor non-conserved amino acid alterations in the conserved domain.

Thus, the genes and nucleotide sequences of the invention include both the naturally occurring sequences as well as derivative or mutant forms. Likewise, the proteins of the invention encompass both naturally occurring proteins as well as variations and modified forms thereof. Such variants will continue to possess the desired MIOX activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequence encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, MIOX activity can be evaluated for these proteins or in other situations as appropriate by assays such as the orcinol assay of Reddy et al. (1981) *J. Biol. Chem.* 256:8510-8518, herein incorporated by reference. MIOX activity can also be measured by determining the reaction product of D-glucuronic acid. See, e.g., Reddy et al. (1981) *J. Biol Chem.* 256: 8510-8518; Mejbaum (1939) *Z. Physiol. Chem.* 258, 117-124; Charalampous et al. (1957) *J. Biol. Chem.,* 228: 1-13.

Variant nucleotide sequences and proteins also encompass sequences and proteins derived from a mutagenic and recombinogenic procedure such as DNA shuffling. With such a procedure, one or more different MIOX coding sequences can be manipulated to create a new MIOX possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the MIOX gene of the invention and other known MIOX genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire MIOX sequence set forth herein or to fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that encode a MIOX protein and which hybridize under stringent conditions to the MIOX sequence disclosed herein, or to fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the MIOX sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire MIOX sequence disclosed herein, or one or more portions thereof, may be used as a probe capable of specifically hybridizing to corresponding MIOX sequences and messenger RNAs. To achieve specific hybridization under a variety of conditions, such probes include sequences that are unique among MIOX sequences and are at least about 10 nucleotides in length, and optimally at least about 20 nucleotides in length. Such probes may be used to amplify corresponding MIOX sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. "Stringent conditions" or "stringent hybridization conditions" is intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA—DNA hybrids, the $T_m$ can be approximated from the equation of Meinkoth and Wahl (1984) *Anal. Biochem.* 138:267-284: $T_m = 81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See ncbi.nlm.nih.gov (a "www" prefix must be used). Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The invention provides for modulating (i.e., increasing or decreasing) MIOX levels in a plant. By modulating the levels of MIOX, the levels of myo-inositol and glucuronate are likewise modulated. The MIOX gene encodes an enzyme that catalyzes myo-inositol oxidation to produce glucuronate. Therefore, increasing levels of MIOX results in decreasing levels of myo-inositol and increasing glucuronate. As MIOX is decreased, myo-inositol is elevated and glucuronate is decreased.

Myo-inositol is essential for embryo development and plays an important role in plant growth and development. Plant structures containing or utilizing MI are involved in structure and function. The first step in MI biosynthesis involves the conversion of D-glucose-6-P to 1L-MI-1-P. Metabolic processing of MI beyond biosynthesis leads to a host of functional roles for the molecule. These roles include: cycling of 1L-MI-1-P and free MI by MI phosphate and MI kinase; oxidation of free MI to D-glucuronic acid with its subsequent role in biogenesis of uronosyl and pentosyl units of pectin, hemicelluloses, and related structures in plant cell walls; esterification of MI to form oxin (IAA) esters and their glycosides; conjugation of free MI with UDP-D-galactose to form galactinol, the galactosyl donor for biosynthesis in the raffinose and galactopinitol series of oligiosaccharides; isommerization and methalation of MI and other isomeric inositols to form o-methyl inositols which participate in stress-related responses, storage of seed products, and production of inositol-glycosides; biosynthesis of phytic acid (MI-$P_6$) and phytic acid pyrophosphates; metabolic recycling of products of phytic acid hydrolysis during phytase-mediated phytic acid dephosphorylation; biosynthesis of phosphatidylinositol, its polyphosphates, and precursors of MI polyphosphate-specific signal transduction; and glycosylated-phosphatidylinositol and glycosylated-inositolphosphorylceramide. Loewus and Murthy (2000) *Plant Science* 150:1-19, herein incorporated by reference. Accordingly, modulation of MIOX levels in a plant or plant embryo can affect any of the functional roles of MI in a plant.

In some embodiments, the MIOX sequences of the present invention are used in combination with other genes and/or proteins that reduce the levels of phytate/phytic acid. In certain aspects of the invention, a second DNA construct comprising a nucleotide sequence that encodes a polypeptide that reduces phytic acid levels in seeds is further stably co-transformed into a plant of interest. Such genes that may be employed for modulation of phytic acid synthesis include phytate biosynthetic genes, particularly myo-inositol monophosphatase-3, myo-inositol 1,3,4-triphosphate5/6 kinase, myo-inositol kinase, or myo-inositol 1-phosphate synthase. See, for example, U.S. Pat. Nos. 6,197,561 and 6,291,224. In a particular embodiment, maize myo-inositol 1-phosphate synthase (SEQ ID NO:3) is used in conjunction with the MIOX sequences of the invention. SEQ ID NO:4 is directed to the amino acid sequence of myo-inositol 1-phosphate synthase.

Methods of the invention involve expression of the coding sequence or antisense sequence of the MIOX gene in plant cells. Expression of the coding sequence may result in increased expression of MIOX gene. Alternatively, antisense expression or cosuppression may be used to decrease expression of the MIOX gene. Antisense constructions, complementary to at least a portion of the messenger RNA (mRNA) for the MIOX sequences of the invention can be constructed.

Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85%, 90%, 95% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85%, 90%, 95% sequence identity, most preferably greater than about 95% sequence identity. See, U.S. Pat. Nos. 5,283,184 and 5,034,323; herein incorporated by reference.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, DNA:RNA vectors, DNA:RNA mutational vectors, DNA:RNA repair vectors, mixed-duplex oligonucleotides, self-complementary DNA:RNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) Proc. Natl. Acad. Sci. USA 96:8774-8778; herein incorporated by reference.

The present invention is also directed to methods of using the sequences described above to affect various properties of agronomic importance in a plant, plant tissue, plant seed, or plant part, including: the MIOX levels; the hemicellulose, pectin, or cellulose content of the cell walls; the digestibility, gum extractability, and milling characteristics; the growth characteristics of a plant; the seed germination characteristics of a plant; and, the seed germination characteristics of a plant, wherein said plant additionally has been modified to have reduced phytic acid levels in its seeds.

Therefore, the invention involves methods for modulating MIOX levels in a plant, plant tissue, plant part, and/or plant seed. As discussed, such modulation can be accomplished by either increasing or decreasing expression of a nucleotide sequence of the invention. Since modulation of MIOX levels has a direct affect on MI levels, the methods of the invention find use in improving various traits or properties of agronomic importance in plants.

The MIOX sequences of the invention can be used to affect the digestibility of a crop plant by altering the content of indigestible components in the plant. For example, arabinoxylans constitute 45%-65% of the grain cell wall, but they impede digestion of the grain and may sequester digestible components of grain, thus reducing digestibility (WO 99/67404; van der Klis et al. (1995) Anim. Feed Sci. Tech. 51:15-27). High levels of such indigestible materials also contribute to the sanitation challenges of livestock and poultry raising (Selinger et al. (1996) Anaerobe 2:263-284). In this regard, the methods of the present invention for modulating MIOX levels can be used to increase the digestibility of grain and forage crops by lowering the concentration of indigestible materials such as hemicelluloses in the modified plant.

"Digestibility" is intended to mean the percentage of a substance taken into a digestive tract that is absorbed by the body. Methods to measure digestibility are known in the art and include, but are not limited to, determining the food conversion ratio (WO 99/67404), sampling chyme for chromium, phosphorous, calcium, magnesium, sodium, and potassium (van der Klis et al. (1995) Anim. Feed Sci. Tech. 51:15-27), in sacco degradation (van Vuuren et al. (1989) Grass & Forage Sci. 44: 223-230), growth studies (Groot Wassink et al. (1989) J. Sci. Food Agric. 46:289-300), and the enzyme digestible dry matter (EDDM) assay (Boisen and Fernandez (1997) Animal Feed Sci. Tech. 68:83-92; and Boisen and Fernandez (1995) Animal Feed Sci. Tech. 51:29-43); all of which are herein incorporated by reference. Such methods can be used to determine the digestibility and/or energy availability of the plant parts of plants modified in accordance with methods of the invention. The modified plants, such as modified grain, may be fed to a variety of livestock including, but not limited to, poultry, cattle, swine, horses, and sheep.

In one embodiment, the methods are useful for modulating the polysaccharide composition of the plant cell walls, specifically the hemicellulose or pectin polysaccharide content of the cell walls of the plant. The predominate polysaccharides in the cell wall of plants include hemicellulose and pectin. "Hemicellulose" includes polysaccharides selected from the group comprised of xylans, glucuronoxylans, arabinoxylans, arabinogalactans II, glucomannans, xyloglucans, mixed-link glucans, and galactomannans. Xylans contain a backbone of (1,4)-linked xylose residues with side chains present in varying amounts. In glucuronoxylans, glucuronic acid side chains predominate, although the compound may contain arabinose and acetyl side chains also. In arabinoxylans, arabinose side chains predominate. Glucomannans contain glucose and xylose linked by 1,4-glycosidic bonds, and galactose side chains are possible. Xyloglucans contain a backbone of (1,4)-linked glucose residues with xylose side chains, although galactose, fucose, and arabinose side chains are possible.

"Pectin" includes polysaccharides rich in galacturonic acid, rhamnose, arabinose, and galactose, such as polygalacturonans, rhamnogalacturonans, and some arabinans, galactans, and arabinogalactans. Polygalacturonans consist primarily of galacturonic acid. Rhamnogalacturonans consist predominantly of galacturonic acid and rhamnose, although some forms may have up to four additional types of sugar. Galactans are polymers of galactose.

In the instant case, the MIOX sequences of the invention may be used to modulate these hemicellulose or pectin polysaccharide components of the plant cell wall. Specifically, MI is a precursor in the formation of hemicellulose and pectin via the MI oxidation pathway, in which MI is converted by MIOX to glucuronate, which is further converted to UDP-glucuronate, a precursor of hemicellulose and pectin. See, e.g., Loewus and Murthy (2000) *Plant Sci.* 150:1-19. Thus, while not bound by any particular theory, it is proposed that modulation of MIOX levels will modulate the amount of MI catabolized via the MI oxidation pathway, thereby likely altering the amount of hemicellulose or pectin polysaccharides present in the cell wall. Reducing MI may result in a reduction in hemicellulose, thereby improving grain processing.

As the proportion of cellulosic to hemicellulosic polysaccharides in the cell wall are controlled by regulating the expression of the MIOX gene, the amount of the cellulose component of the cell wall can be altered by the methods of the invention. Specifically, cellulose is formed via the UDP-glucose metabolic pathway, with UDP-glucose itself formed from glucose-6-phosphate. Because glucose-6-phosphate is also the substrate for MI formation, inhibition of MIOX can be expected to decrease the amount of carbon flowing into the cell walls from the MI oxidation pathway, and increase the amount of carbon entering the cell walls via the UDP-glucose pathway, i.e., increase the amount of cellulose in the cell walls.

In another embodiment, the methods of the invention can be used for improving gum extractability. "Gum" is intended to mean any of numerous colloidal polysaccharides of plant origin that are gelatinous when moist but which harden on drying, including, but not limited to, arabinoxylans, galactans, and mixed-link glucans. Whereas high gum concentration can be detrimental to digestibility, there is a strong interest in their industrial applications, such as their use as thickeners in the food industry (Sanderson (1982) *Prog. Food Nutr. Sci.* 6:77-87). About 15% of the total corn produced in the USA is subjected to wet milling to produce mainly starch and also oil from the germ. Wet milling is a multi-step process involving the steeping and grinding of kernels, and separating the kernels into starch, protein, oil, and fiber portions. See S. R. Eckhoff (1992) *Proceedings of the 4th Corn Utilization Conference*, Jun. 24-26, 1992, St. Louis, Mo., (National Corn Growers Association, CIBA-GEIGY Seed Division, and the USDA). The fiber residue left at the end of the wet-milling process is rich in arabinoxylans. However, it is not currently economically feasible to extract arabinoxylans from the wet-milled residue of corn. By modulating MIOX levels, the level of arabinoxylans, galactans, or mixed-link glucans can be increased improving gum extractability.

In light of the ability to alter plant cell wall composition by modulating MIOX levels, the present invention may also be used to improve the milling characteristics of a crop plant or a part thereof. Specifically, changes in cell wall polysaccharide composition can be used to improve the ability of cells to fracture or rupture upon milling, thereby improving the milling characteristics of the crop plant. Various methods of ethanol dry grind are known in the art. See, for example, U.S. Pat. No. 6,592,921, U.S. Pat. No. 6,433,146, Taylor et al. (2003) *Appl. Biochem. Biotechnol.* 104:141-148; Taylor et al. (2000) *Biotechnol. Prog.* 16:541-7, and Taylor et al. (2001) *Appl. Biocehm. Biotechnol.* 94:41-9. Methods of wet milling are also known in the art. See, for example, Anderson et al. (1982) "*The Corn Milling Industry*"; *CRC Handbook of Processing and Utilization in Agriculture*, A. Wolff, Boca Raton, Fla., CRC Press., Inc., Vol. 11, Part 1, *Plant Products:* 31-61 and Eckhoff (Jun. 24-26, 1992) *Proceedings of the 4th Corn Utilization Conference*, St. Louis, Mo., printed by the National Corn Growers Association, CIBA-GEIGY Seed Division, and the USDA, both of which are herein incorporated by reference.

The present invention also provides a method for modulating the plant growth rate. Plant cell growth is accomplished through loosening of the plant cell wall and expansion due to the turgor pressure of the plant cell. There is a relationship between the looseness of the plant cell wall and the turgor pressure of the cell such that looser cell walls require less turgor pressure to expand, while stronger cell walls require more turgor pressure to expand. A component of cell wall loosening is the deposition by a process known as intussusception of matrix polysaccharides within the cell wall. The newly incorporated polysaccharides relieve stress in the load-bearing components of the plant cell wall and prevent a perpetual gradual thinning of the cell walls during plant cell growth. Under conditions of drought or stress, the turgor pressure of the cell decreases, and the plant decreases synthesis of the polysaccharides necessary for cell-wall loosening and cell growth. See Ray (1992) *Curr. Topics in Plant Biochem. & Phys.* 11:18-41. In this manner, the interplay between low turgor pressure and the strength of the cell wall prevents or slows growth. Increased synthesis of polysaccharides would allow the plant cell wall to loosen and allow growth with less turgor pressure. Therefore, plant cell growth may be modulated by modulating MIOX levels in order to modulate such polysaccharide levels. Although modulated growth of the entire plant is one possible desired embodiment, it is recognized that modulated growth of a specific tissue may be desired. Thus, the sequences of the invention can be used with tissue-preferred promoters.

The methods of the invention can also be used for modulating seed germination in a plant. MI plays an important role in plant growth and development, and is essential for plant embryo development. Therefore, modulation of MIOX levels may modulate MI levels and thereby affect seed germination. For the modulation of seed germination, modulation in a seed- or embryo-preferred manner is advantageous.

The MIOX sequences of the invention can also be used to modulate MI levels in plants that have reduced seed phytic acid levels. Phytic acid is a compound that has a variety of anti-nutritive effects, and which is a source of surface and ground water pollution when present in animal waste. It has been proposed that a sequential ATP-dependent phosphorylation of Ins(3)P leads to phytic acid production in developing seeds. See, for example, Shi et al. (2003) *Plant Physiol* 131:507-515. One gene involved in the biosynthesis of phytic acid is inositol phosphate kinase. SEQ ID NOs:5 and 6 comprise the nucleotide and amino acid sequences for maize inositol phosphate kinase (ZM-IPK), respectively. Reduced phytic acid is a desired goal for genetic improvement in several crops. Thus, a variety of methods have been proposed for reducing seed phytic acid levels via reducing the levels of one or more of the compounds in its biosynthetic pathway, for example by decreasing the activity of the enzyme 1D-myo-inositol 3-phosphate synthase (mi1ps; synonymously MIPS, 1L-myo-inositol 1-phosphate synthase, or EC 5.5.1.4; SEQ ID NO:4) that converts glucose-6-phosphate (G-6-P) to 1D-myo-inositol 3-phosphate (Ins(3)P; synonymously 1L-myo-inositol 1-phosphate), a precursor for phytic acid. See, e.g., U.S. Pat. Nos. 6,197,561 and 6,291,224; and U.S. Patent Application No. 20030079247. Decreasing the activity of the enzyme 1D-myo-inositol 3-phosphate synthase can reduce phytic acid, but it also reduces MI content. By decreasing MIOX in an embryo-specific manner, MI oxidation is reduced, thereby increasing the MI available for normal embryo development. Thus, the methods of the invention can be used in combination with mi1ps cosuppression.

MI is a precursor for phytic acid biosynthesis in plant seeds. Increasing MIOX activity can reduce MI flowing into the phytic acid pathway, therefore reducing phytic acid synthesis in plants. Overexpression of MIOX can be combined with cosuppression of other phytic acid genes, such as myo-inositol kinase, Ins(1,3,4)$P_3$ 5/6-kinase, Ins(1,3,4,5,6)$P_5$ 2-kinase, to reduce phytic acid in plants.

Phytic acid levels in seed may be reduced by mutations to or suppression of enzymes in the biosynthetic pathway leading to phytic acid, because MI is part of this pathway, such changes can also reduce MI levels, and therefore adversely impact seed germination. Therefore, the MIOX sequence of the present invention may be used to modulate MIOX levels in the plant, thereby modulating MI catabolism to insure an adequate supply of MI for germination in conditions of low seed phytic acid production.

It is recognized that in addition to using the methods of the invention in plants having mi1ps cosuppression, the compositions of the invention can be used in combination with other sequences useful for reducing phytic acid content in a plant. For example, the MIOX sequences of the invention can be used with other sequences such as the maize mi1ps nucleotide sequence (accession number AF056326; SEQ ID NO:3), the 1pa2 nucleotide sequence (Shi et al. (2003) *Plant Physiol* 131:507-515) herein incorporated by reference.

The MIOX sequences of the invention may be used in expression cassettes or DNA constructs designed for expression in the plant of interest. The cassette will include 5' and 3' regulatory sequences operably linked to a MIOX sequence of the invention. "Operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the MIOX sequence to be under the transcriptional regulation of the regulatory regions.

The expression cassette may additionally contain selectable marker genes for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

The expression cassette will include in the 5'-3' direction of transcription, a transcriptional and translational initiation region (i.e., a promoter), a MIOX DNA sequence of the invention, and a transcriptional and translational termination region (i.e., termination region) functional in plants. The promoter may be native or analogous, or foreign or heterologous, to the plant host and/or to the MIOX DNA sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the MIOX DNA sequence of the invention, it is intended that the promoter is not the native or naturally occurring promoter for the operably linked MIOX DNA sequence of the invention. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of the MIOX protein of the invention in the plant or plant cell. Thus, the phenotype of the plant or plant cell is altered.

The termination region may be native with the transcriptional initiation region, may be native with the operably linked MIOX DNA sequence of interest, may be native with the plant host, or may be derived from another source (i.e., foreign or heterologous to the promoter, the MIOX DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, N.Y.), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. For example, the nucleic acids of the invention may be combined with constitutive, tissue-preferred, or other promoters for expression in plants.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529, both of which are herein incorporated by reference). Gamma-zein is a preferred endosperm-specific promoter. Glb-1 is a preferred embryo-specific promoter. See, for example, Yang et al. (2001) *Proc. Natl. Acad. Sci. U. S. A.* 98(20):11438-43; herein incorporated by reference. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by progeny thereof. "Transient transformation" is intended to mean that a nucleotide construct introduced into a plant does not integrate into the genome of the plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886, 244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322, 783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the MIOX sequences of the invention can be provided to a plant using a variety of transient transformation methods. Such transient transformation methods include, but are not limited to, the introduction of the MIOX protein or variants and fragments thereof directly into the plant or the introduction of the a MIOX transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the MIOX polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which its released to become integrated into the genome is greatly reduced. Such methods include the use particles coated with polyethylimine (PEI; Sigma #P3143).

The nucleotide constructs of the invention may be introduced into plants by contacting plants with a virus or viral nucleic acids. Generally, such methods involve incorporating a nucleotide construct of the invention within a viral DNA or RNA molecule. It is recognized that the MIOX protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant have stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

In certain embodiments the polynucleotides of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723, 756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885, 802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No.

5,792,931); avirulence and disease resistance genes (Jones et al. (1994) *Science* 266:789; Martin et al. (1993) *Science* 262: 1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference. Examples of additional genes that can be stacked with the polynucleotides of the present invention include any single or multiple combination of genes that affect the level and/or composition of oil produced in the plant (eg., Agp2, Lec1, HGGT, Fad); genes that affect the level and/or composition of cell wall materials produced in the plant (eg., UDPGDH, RGP, CesA); genes that affect the level of phytic acid in seed (eg., Lpa1, Lpa2, etc); genes that affect the digestibility and/or amino acid composition of protein occurring within seed (eg., CS27, BHL9); genes that affect the average size of starch granules occurring within plants (eg., Ole; FtsZ; Bt1, etc.).

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Pedigree breeding starts with the crossing of two genotypes, such as an elite line of interest and one other elite inbred line having one or more desirable characteristics (i.e., having stably incorporated a polynucleotide of the invention, having a modulated activity and/or level of the polypeptide of the invention, etc) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→F5, etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line of interest, comprising the steps of crossing a plant of maize inbred line of interest with a donor plant comprising a mutant gene or transgene conferring a desired trait (i.e., MIOX activity), selecting an F1 progeny plant comprising the mutant gene or transgene conferring the desired trait, and backcrossing the selected F1 progeny plant to the plant of maize inbred line of interest. This method may further comprise the step of obtaining a molecular marker profile of maize inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development" Fehr, 1993 Macmillan Publishing Company the disclosure of which is incorporated herein by reference. In addition, mutations created in other lines may be used to produce a backcross conversion of elite lines that comprises such mutations.

The effects of transformation on the expression of the introduced MIOX sequences of the present invention may be assayed in a variety of ways. Differences in the expression of specific genes between, for example, an untransformed state and a transformed state where the plant now contains introduced MIOX sequences may be determined using gene expression profiling. Total RNA or mRNA may be analyzed using the gene expression profiling process (GeneCalling®) as described in U.S. Pat. No. 5,871,697, herein incorporated by reference.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Optimally, plants of the present invention are crop plants (for example, corn, alfalfa, sunflower, *Brassica*, soybean, cotton, safflower, peanut, *sorghum*, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, *sorghum*, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The article "a" and "an" are used herein to refer to one or more than one (i.e., to at least one) of the grammatical object of the article. By way of example, "an element" means one or more element.

The following examples are offered by way of illustration and not by way of limitation.

EXPERIMENTAL

Example 1

Transformation and Regeneration of Transgenic Plants

Immature maize embryos from greenhouse donor plants are bombarded with a plasmid containing the MIOX sequence of the present invention operably linked to the desired promoter and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the MIOX sequence of the present invention operably linked to the desired promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for the presence of the MIOX sequence using any method known to the skilled artisan, e.g., direct detection of the MIOX sequence DNA or by screening for introduced MIOX activity.

Bombardment and Culture Media

Bombardment medium (560Y) comprises 4.0 g/l N6 basal salts (SIGMA C-1416), 1.0 mill Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 2

*Agrobacterium*-mediated Transformation

For *Agrobacterium*-mediated transformation of maize with a MIOX sequence of the present invention, optimally the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the MIOX sequence of the present invention to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). Optimally the immature embryos are cultured on solid medium following the infection step. Following this co-cultivation period an optional "resting" step is contemplated. In this resting step, the embryos are incubated in the presence of at least one antibiotic known to inhibit the growth of *Agro-*

*bacterium* without the addition of a selective agent for plant transformants (step 3: resting step). Optimally the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Optimally, the immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 3

Soybean Embryo Transformation

Soybean embryos are bombarded with a plasmid containing the MIOX sequence of the present invention operably linked to the desired promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature (London)* 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the MIOX sequence of the present invention operably linked to the desired promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl CaCl$_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 4

Sunflower Meristem Tissue Transformation

Sunflower meristem tissues are transformed with an expression cassette containing the MIOX sequence of the present invention operably linked to the desired promoter as follows (see also European Patent Number EP 0 486233, herein incorporated by reference, and Malone-Schoneberg et al. (1994) *Plant Science* 103:199-207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al. (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473-497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA$_3$), pH 5.6, and 8 g/l Phytagar.

The explants are subjected to microprojectile bombardment prior to *Agrobacterium* treatment (Bidney et al. (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the MIOX sequence of the present invention operably linked to the desired promoter is introduced into *Agrobacterium* strain EHA105 via freeze-thawing as described by Holsters et al. (1978) *Mol. Gen. Genet.* 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for MIOX activity as described elsewhere herein.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by MIOX activity analysis of leaf extracts while transgenic seeds harvested from NPTII-positive $T_0$ plants are identified by MIOX activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 µg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under 16-hour day and 26° C. incubation conditions.

Explants (around 2 cm long) from two weeks of culture in 374C medium are screened for MIOX activity using assays described elsewhere herein. After positive (i.e., for MIOX expression) explants are identified, those shoots that fail to exhibit MIOX activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for MIOX expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil.

In the first two weeks, they are maintained under high humidity conditions to acclimatize to a greenhouse environment.

Example 5

Determination of Phytic Acid, myo-Inositol and Inorganic Phosphate Inorganic Phosphate Assay A rapid test was used to assay inorganic phosphate content in kernels. Individual kernels were placed in a 25-well plastic tray and crushed at 2000 psi using a hydraulic press. Two milliliters of 1N $H_2SO_4$ were added into each sample and incubated at room temperature for 2 hr. Four milliliters of 0.42% ammonium molybdate-1N $H_2SO_4$:10% ascorbic acid (6:1) was added. In the case of an increased inorganic phosphate content, blue color developed in 20 min. Non-mutant kernels served as a negative control and mutant lpa2 kernels as a positive control.

Determination of Phytic Acid and Inorganic Phosphate

Phytic acid and inorganic phosphate in dry, mature seeds were assayed according to modifications of the methods described by Haug and Lantzsch (1983) and Chen et al. (1956), respectively. Single kernels were ground using a Geno/Grinder2000 (Sepx CertiPrep, Metuchen, N.J.). Twenty-five to thirty-five milligram samples were placed into 1.5-ml Eppendoff tubes. One milliliter of 0.4 N HCl was added, and the tubes were shaken on a gyratory shaker at room temperature for 3.5 hours. The tubes were then centrifuged at 3,900 g for 15 min. Supernatants were transferred into fresh tubes and used for both phytic acid and inorganic phosphate determinations. Measurements were performed in duplicate. For phytic acid assay, 35 µl of each extract was placed into wells of a 96-well microtiter plate. Thirty-five microliters of distilled $H_2O$ and 140 □l of 0.02% ammonium iron(III) sulphate-0.2 N HCl were added to each sample. The plate was covered with a rubber lid and heated in a thermalcycler at 99° C. for 30 min. The plate was cooled to 4° C., kept on an ice-water bath for 15 min, and then left at room temperature for 20 min. The plate was sealed with sticky foil and centrifuged at 3,900 g at 24° C. for 30 min. Eighty microliters of each supernatant were placed into wells of a fresh 96-wellplate, 120 µl of 1% 2,2'-bipyridine-1% thioglycollic acid was added to each well, and then absorbance was recorded at 519 nm using a VERSAmax™ micro plate reader (Molecular Devices, Sunnyvale, Calif.). Phytic acid content is presented as phytic acid phosphorus (PAP). Authentic phytic acid (Sigma, P-7660) served as a standard. The phytic acid assay may also measure $InsP_5$ and $InsP_4$ if they present in samples. To determine inorganic phosphate, 200 µl of each extract was placed into wells of a 96-well microtiter plate. One hundred microliters of 30% aqueous trichloroacetic acid was added to each sample, and the plates were shaken and centrifuged at 3,900 g for 10 min. Fifty microliters of each supernatant were transferred into a fresh plate and 100 µl of 0.42% ammonium molybdate-1N $H_2SO_4$:10% ascorbic acid (7:1) was added. The plates were incubated at 37° C. for 30 min and then absorbance at 800 nm was measured. Potassium phosphate was used as a standard. Inorganic phosphate content is presented as inorganic phosphate phosphorus.

Determination of Seed myo-Inositol myo-Inositol was quantified in dry, mature seeds and excised embryos. Tissue was ground as above and mixed thoroughly. One hundred milligram samples were placed into 7-ml scintillation vials. One milliliter of 50% aqueous ethanol was added and the vials were shaken on a gyratory shaker at room temperature for 1 hour. Extracts were decanted through a 0.45 µm nylon syringe filter attached to a 1-ml syringe barrel. Residues were re-extracted with 1 ml fresh 50% aqueous ethanol and the second extracts were filtered as before. The two filtrates were combined in a 10×75 mm glass tube and evaporated to dryness in a speedvac (Savant). The myo-inositol derivative was produced by redissolving the residues in 50 µl of pyridine and 50 µl of trimethylsilylimadazole: trimethylchlorosilane (100:1) (Tacke & Casper, 1996). The silylation reaction is compromised if a precipitate appears at this stage. The tubes were capped and incubated at 60° C. for 15 min. One milliliter 2,2,4-trimethylpentane and 0.5 ml distilled water were added to each sample, and each was vortexed and then centrifuged at 1,000 g for 5 min. The upper organic layers were transferred with pasteur pipettes into a 2-ml glass autosampler vial and crimp capped. myo-Inositol, as hexa-trimethylsilyl ethers, was quantified with an Agilent model 5890 gas chromatograph coupled with an Agilent model 5972 mass spectrometer. Measurements were performed in triplicate. One microliter samples were introduced in the splitless mode onto an Agilent 30 m×0.25 mm i.d.×0.25 µm film thickness 5MS column. The initial oven temperature of 70° C. was held for 2 min after which it was increased at 25° C. $min^{-1}$ to 170° C., then at 5° C. $min^{-1}$ to 215° C., then finally at 25° C. $min^{-1}$ to 250° C. at which it was held for 5 min. The inlet and transfer line temperatures were 250° C. Helium at a constant flow of 1 $min^{-1}$ was the carrier gas. Electron impact mass spectra from m/z 50-560 were acquired at −70 eV after a 5-min solvent delay. The myo-inositol derivative was well resolved from other peaks in the total ion chromatograms. Authentic myo-inositol standards in aqueous solutions were dried, derivatized, and analyzed at the same time. Regression coefficients of four-point calibration curves were typically 0.999-1.000.

Example 6

Determination of myo-Inositol Oxygenase Activity

The enzyme activity can be measured by determining the reaction product of D-glucuronic acid (see, for example, Reddy et al. (1981). *J. Biol. Chem.* 256: 8510-8518). The reaction mixture contains 50 mM Tris.HCl (pH 8.0), 2.0 mM L-cystein, 1.0 mM ferrous ammonium sulfate and 60 mM myo-inositol, and is pre-incubated at 30° C. for 5 min. The reaction is initiated by adding appropriate quantities of enzyme, allowed to proceed with shaking in an air atmosphere for 15 min. at 30° C. (i.e., the reaction needs oxygen), and terminated by adding 30% trichloroacetic acid to a final concentration of 10%. After removal of the precipitated protein by centrifugation, the amount of D-glucuronic acid is quantified by colorimetric assay based on the reaction of orcinol with D-glucuronic acid (See, for example, Mejbaum (1939) *J. Physiol. Chem.* 258:117-124; Charalampous and Chryssoula (1957). *J. Biol. Chem.* 228:1-13).

Example 7

Analysis of Cell Wall Polysaccharide Composition

A known amount of dry, powdered tissue is placed into a 2 ml eppendorf tube. Typical amounts of tissue analyzed are 50 mg for isolated endosperm or germ tissue, and 20 mg for pericarp. Free sugars are extracted from the tissue by incubating the samples with constant mixing at 80° C. with 1 ml of 80% (v/v) ethanol for 15 minutes. The samples are centrifuged (14,000×g) for 5 minutes and the supernatant removed and discarded. The resulting pellet is washed twice with 1 ml 80% ethanol each time, by vortexing the sample, centrifuging as above, and discarding the supernatant. The pellet is washed a final time with 1 mL of acetone and allowed to air dry before destarching.

Added to the dry pellet for destarching is 0.3 mL of 300 U/assay amylase in a MOPS buffer [50 mM MOPS (pH 7.0), 5 mM $CaCl_2$, 0.02% Na-azide]. The samples are incubated at 90° C. for 10 minutes with constant mixing. Samples are cooled to 55° C. before adding 0.2 mL of 285 mM Na-acetate containing the enzyme, amyloglucosidase (equiv. of 20 U/assay). This enzymatic reaction is conducted overnight at 55° C. and with constant mixing.

Following destarching, add 1.2 mL of absolute ethanol and cool the samples on ice for 1 hour to precipitate remaining polysaccharides. Centrifuge samples as above for 10 minutes and discard the supernatant. Wash samples twice with 1 mL of 80% (v/v) ethanol, centrifuging and discarding the supernatant as already described. Finally, wash the samples with 1 mL of acetone, centrifuge, discard the supernatant, and allow the samples to air dry.

To hydrolyze the precipitated cell wall polysaccharides, add 1.5 mL of 2 N $H_2SO_4$ and vigorously vortex the samples until they are fully mixed. Incubate the samples at 100° C. for 30 minutes. Cool samples on ice and centrifuge as above for 10 minutes. One mL of the supernatant is removed for separation and quantitation of released sugars by high-performance anion-exchange chromatography using pulsed amperomeric detection.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. An isolated nucleic acid molecule comprising a nucleotide sequence selected from the group consisting of:
   a) the nucleotide sequence set forth in SEQ ID NO:1;
   b) a nucleotide sequence encoding the amino acid sequence set forth in SEQ ID NO:2; and
   c) a nucleotide sequence complementary to the full-length nucleotide sequence set forth in (a) or (b).

2. A nucleotide construct comprising the nucleic acid molecule of claim 1 operably linked to a promoter that drives expression in a plant cell.

3. An expression cassette comprising the nucleotide construct of claim 2.

4. A plant cell comprising at least one nucleotide construct that comprises the nucleic acid molecule of claim 1 operably linked to a promoter that drives expression in a plant cell, wherein the nucleotide construct is stably incorporated into the genome of the plant cell.

5. A plant comprising at least one nucleotide construct that comprises the nucleic acid molecule of claim 1 operably linked to a promoter that drives expression in a plant cell.

6. The plant of claim 5, wherein the nucleotide construct is stably incorporated into the genome of the plant.

7. The plant of claim 6, wherein said plant is a dicot.

8. The plant of claim 6, wherein said plant is a monocot.

9. The plant of claim 8, wherein said monocot is selected from the group consisting of maize, *sorghum*, barley, rice, and wheat.

10. The plant of claim 6, wherein said promoter is selected from the group consisting of a tissue-preferred promoter, a seed-preferred promoter, and an embryo-specific promoter.

11. Transgenic seed of the plant of claim 6, wherein the seed comprises the nucleotide construct.

* * * * *

SEQUENCE LISTING

```
<160> NUMBER OF SEQ ID NOS: 9

<210> SEQ ID NO 1
<211> LENGTH: 1265
<212> TYPE: DNA
<213> ORGANISM: Zea mays

<400> SEQUENCE: 1
gaattcccgg gtcgacccac gcgtccggtt gccgtagccg tgttcttgga ctctgttacg      60
tgctgccatt ttgccaaggc tagccccctc ctcctcttct tcctcttctt cttttcgcga     120
cgatcagaga agaagatgac gatcaccatt gaacagcccc agctcgatgc ggtggcggag     180
aggaaagtcc ccggcggagg tgaccccgcg gagctggtgc tcgacgccgg cttcgtcgtg     240
ccggacgcca acgccttcgg caataccttc agggactacg acgcggagtc ggagcggaag     300
cagacggtag aggagttcta ccgggtgaac cacgtgaggc agacgcacga gttcgtggcg     360
cggatgcggg cggagtacgg gcggctggac aagacggaga tgggcatctg ggagtgcatc     420
gagctgctga acgagttcat cgacgacagc gacccggacc tggacatgcc ccagatcgag     480
cacctgctgc agaccgccga ggccatccgc aaggactacc ccgacgagga ctggctccac     540
ctcaccggac tcatccacga cctgggcaag gtgctgctgc acccaagctt cggggagctc     600
cctcagtggg ctgtcgtcgg tgacaccttc cccgtcggct gcgcatacga cgagtgcaac     660
gtccacttca agtacttcaa ggagaacccc gactaccaca acccgaagct caacaccaag     720
ttgggggtct actcggaggg ctgcggcctc aacaaggtgc tcatgtcatg gggccacgac     780
gactacatgt acctggtggc caaggagaac aagtgcaccc ttccttccgc ggggctgttc     840
atcatcagat accactcgtt ctaccccctg cacaagcatg gagcctacac acacctgatg     900
gacgatgagg acaaggagaa cctcaagtgg ctgcatgtgt tcaacaagta tgacctgtac     960
agcaagagca acagcaggat cgacgtggag gaggtgaagc cctactacat gtccctaatc    1020
gacaagtact tcccggccaa gctaagatgg tgagaagggg cggcctggcc tggacctgga    1080
tggatggaac cccaaggccc caccaagagc tgtcgttcca agtgtccatg taccatatac    1140
atatatatag actacgaata cagtatgtgt gccatgtacg gtcatttttt tttacagagt    1200
tgagaggagt acccatgccg tttcgaataa aagttgcctg cgtttgttcc aaagaaaaaa    1260
aaaaa                                                                1265

<210> SEQ ID NO 2
```

<211> LENGTH: 305
<212> TYPE: PRT
<213> ORGANISM: Zea mays

<400> SEQUENCE: 2

Met Thr Ile Thr Ile Glu Gln Pro Gln Leu Asp Ala Val Ala Glu Arg
 1               5                  10                  15

Lys Val Pro Gly Gly Asp Pro Ala Glu Leu Val Leu Asp Ala Gly
             20                  25                  30

Phe Val Pro Asp Ala Asn Ala Phe Gly Asn Thr Phe Arg Asp Tyr
         35                  40                  45

Asp Ala Glu Ser Glu Arg Lys Gln Thr Val Glu Phe Tyr Arg Val
     50                  55                  60

Asn His Val Arg Gln Thr His Glu Phe Val Ala Arg Met Arg Ala Glu
 65                  70                  75                  80

Tyr Gly Arg Leu Asp Lys Thr Glu Met Gly Ile Trp Glu Cys Ile Glu
                 85                  90                  95

Leu Leu Asn Glu Phe Ile Asp Asp Ser Asp Pro Asp Leu Asp Met Pro
                100                 105                 110

Gln Ile Glu His Leu Leu Gln Thr Ala Glu Ala Ile Arg Lys Asp Tyr
            115                 120                 125

Pro Asp Glu Asp Trp Leu His Leu Thr Gly Leu Ile His Asp Leu Gly
    130                 135                 140

Lys Val Leu Leu His Pro Ser Phe Gly Glu Leu Pro Gln Trp Ala Val
145                 150                 155                 160

Val Gly Asp Thr Phe Pro Val Gly Cys Ala Tyr Asp Glu Cys Asn Val
                165                 170                 175

His Phe Lys Tyr Phe Lys Glu Asn Pro Asp Tyr His Asn Pro Lys Leu
            180                 185                 190

Asn Thr Lys Leu Gly Val Tyr Ser Glu Gly Cys Gly Leu Asn Lys Val
        195                 200                 205

Leu Met Ser Trp Gly His Asp Asp Tyr Met Tyr Leu Val Ala Lys Glu
    210                 215                 220

Asn Lys Cys Thr Leu Pro Ser Ala Gly Leu Phe Ile Ile Arg Tyr His
225                 230                 235                 240

Ser Phe Tyr Pro Leu His Lys His Gly Ala Tyr Thr His Leu Met Asp
                245                 250                 255

Asp Glu Asp Lys Glu Asn Leu Lys Trp Leu His Val Phe Asn Lys Tyr
            260                 265                 270

Asp Leu Tyr Ser Lys Ser Asn Ser Arg Ile Asp Val Glu Glu Val Lys
        275                 280                 285

Pro Tyr Tyr Met Ser Leu Ile Asp Lys Tyr Phe Pro Ala Lys Leu Arg
    290                 295                 300

Trp
305

<210> SEQ ID NO 3
<211> LENGTH: 1665
<212> TYPE: DNA
<213> ORGANISM: Zea mays

<400> SEQUENCE: 3
agcctccttc ctcctctcac tctcgctcgc gctgcctcgc tacctcgctt cgcattccat      60
tcgaaaagag gggaggaaag gcaagatgtt catcgagagc ttccgcgtcg agagccccca     120
cgtgcggtac ggcccgatgg agatcgagtc ggagtaccgg tacgacacga cggagctggt     180

-continued

```
acacgagggc aaggacggcg cctcacgctg ggtcgtccgc cccaagtccg tcaagtacaa    240
cttccggacc agaaccgccg tccccaagct cggggtgatg cttgtggggt ggggaggcaa    300
caacgggtcc acgctgacgg ctggggtcat tgccaacagg gagggatct  catgggcgac    360 caaggacaag gtgcagcaag ccaactacta cggctccctc acccaggcct ccaccatcag    420
agtcggcagc tacaacgggg aggagatcta tgcgccgttc aagagcctcc ttcccatggt    480
gaacccagac gacattgtgt tcggaggctg ggacattagc aacatgaacc tggccgactc    540
catgaccagg gccaaggtgc tggatattga cctgcagaag cagctcaggc cctacatgga    600
gtccatggtg ccacttcccg gtatctatga tccggacttc atcgcggcta accagggctc    660
tcgcgccaac agtgtcatca agggcaccaa gaaagaacag gtggagcaga tcatcaagga    720
tatcagggag tttaaggaga agaacaaagt ggacaagata gttgtgttgt ggactgcaaa    780
cactgaaagg tatagcaatg tgtgcgctgg tctcaacgac acgatggaga atctactggc    840
atctgtggac aagaacgagg cggaggtatc accatcaaca ctatatgcca ttgcctgtgt    900
catggagggg gtgccgttca tcaatgggag cccccagaac accttttgtgc ctgggctgat    960 tgatcttgct ataaaaaaca actgcttgat tggtggtgac gacttcaaga gtggacagac   1020
caagatgaaa tctgtcttgg tcgatttcct tgttggtgct ggaataaagc ccacctcaat   1080
cgtgagctac aaccacttgg gaaacaacga tggcatgaac ctgtctgccc ctcaagcatt   1140
caggtccaag gagatctcca agagcaacgt ggtggatgac atggtctcga gcaatgccat   1200
cctctatgag cccggcgagc atcccgatca tgtcgttgtc atcaagtatg tgccgtacgt   1260
gggagacagc aagagggcta tggacgagta cacctcagag atcttcatgg gcggcaagaa   1320
caccatcgtg ctgcacaaca cctgtgagga ctcgctcctc gccgcaccta tcatccttga   1380
tctggtgctc ttggctgagc tcagcaccag gatccagctg aaagctgagg gagaggacaa   1440
attccactcc ttccacccgg tggccaccat cctgagctac ctcaccaagg cacccctggt   1500 tcccccctggc acaccggtgg tgaacgctct ggccaagcag agggcgatgc tggagaacat   1560
catgagggcc tgcgttgggc tggccccaga gaacaacatg atcctggagt acaagtgagc   1620
caagtggcgt gccctgcagc gcgaggttag ctgctggaag ggaac                  1665
```

<210> SEQ ID NO 4
<211> LENGTH: 510
<212> TYPE: PRT
<213> ORGANISM: Zea mays

<400> SEQUENCE: 4

```
Met Phe Ile Glu Ser Phe Arg Val Glu Ser Pro His Val Arg Tyr Gly
  1               5                  10                  15

Pro Thr Glu Ile Glu Ser Glu Tyr Arg Tyr Asp Thr Thr Glu Leu Val
                 20                  25                  30

His Glu Gly Lys Asp Gly Ala Ser Arg Trp Val Val Arg Pro Lys Ser
             35                  40                  45

Val Lys Tyr Asn Phe Arg Thr Arg Thr Ala Val Pro Lys Leu Gly Val
         50                  55                  60

Met Leu Val Gly Trp Gly Gly Asn Asn Gly Ser Thr Leu Thr Ala Gly
 65                  70                  75                  80

Val Ile Ala Asn Arg Glu Gly Ile Ser Trp Ala Thr Lys Asp Lys Val
                 85                  90                  95

Gln Gln Ala Asn Tyr Tyr Gly Ser Leu Thr Gln Ala Ser Thr Ile Arg
            100                 105                 110
```

-continued

```
Val Gly Ser Tyr Asn Gly Glu Glu Ile Tyr Ala Pro Phe Lys Ser Leu
            115                 120                 125

Leu Pro Met Val Asn Pro Asp Asp Ile Val Phe Gly Gly Trp Asp Ile
        130                 135                 140

Ser Asn Met Asn Leu Ala Asp Ser Met Thr Arg Ala Lys Val Leu Asp
145                 150                 155                 160

Ile Asp Leu Gln Lys Gln Leu Arg Pro Tyr Met Glu Ser Met Val Pro
                165                 170                 175

Leu Pro Gly Ile Tyr Asp Pro Asp Phe Ile Ala Ala Asn Gln Gly Ser
            180                 185                 190

Arg Ala Asn Ser Val Ile Lys Gly Thr Lys Glu Gln Val Glu Gln
        195                 200                 205

Ile Ile Lys Asp Ile Arg Glu Phe Lys Glu Lys Asn Lys Val Asp Lys
    210                 215                 220

Ile Val Val Leu Trp Thr Ala Asn Thr Glu Arg Tyr Ser Asn Val Cys
225                 230                 235                 240

Ala Gly Leu Asn Asp Thr Met Glu Asn Leu Leu Ala Ser Val Asp Lys
            245                 250                 255

Asn Glu Ala Glu Val Ser Pro Ser Thr Leu Tyr Ala Ile Ala Cys Val
                260                 265                 270

Met Glu Gly Val Pro Phe Ile Asn Gly Ser Pro Gln Asn Thr Phe Val
            275                 280                 285

Pro Gly Leu Ile Asp Leu Ala Ile Lys Asn Asn Cys Leu Ile Gly Gly
        290                 295                 300

Asp Asp Phe Lys Ser Gly Gln Thr Lys Met Lys Ser Val Leu Val Asp
305                 310                 315                 320

Phe Leu Val Gly Ala Gly Ile Lys Pro Thr Ser Ile Val Ser Tyr Asn
                325                 330                 335

His Leu Gly Asn Asn Asp Gly Met Asn Leu Ser Ala Pro Gln Thr Phe
            340                 345                 350

Arg Ser Lys Glu Ile Ser Lys Ser Asn Val Val Asp Asp Met Val Ser
        355                 360                 365

Ser Asn Ala Ile Leu Tyr Glu Pro Gly Glu His Pro Asp His Val Val
370                 375                 380

Val Ile Lys Tyr Val Pro Tyr Val Gly Asp Ser Lys Arg Ala Met Asp
385                 390                 395                 400

Glu Tyr Thr Ser Glu Ile Phe Met Gly Gly Lys Asn Thr Ile Val Leu
            405                 410                 415

His Asn Thr Cys Glu Asp Ser Leu Leu Ala Ala Pro Ile Ile Leu Asp
        420                 425                 430

Leu Val Leu Leu Ala Glu Leu Ser Thr Arg Ile Gln Leu Lys Ala Glu
    435                 440                 445

Gly Glu Asp Lys Phe His Ser Phe His Pro Val Ala Thr Ile Leu Ser
        450                 455                 460

Tyr Leu Thr Lys Ala Pro Leu Val Pro Pro Gly Thr Pro Val Val Asn
465                 470                 475                 480

Ala Leu Ala Lys Gln Arg Ala Met Leu Glu Asn Ile Met Arg Ala Cys
            485                 490                 495

Val Gly Leu Ala Pro Glu Asn Asn Met Ile Leu Glu Tyr Lys
        500                 505                 510

<210> SEQ ID NO 5
<211> LENGTH: 1428
```

```
<212> TYPE: DNA
<213> ORGANISM: Zea mays

<400> SEQUENCE: 5
ccacgcgtcc gcaaatttca atctccatcg atcgattcct cccgaacccg acccgatggc      60
ctccgacgcc gccgccgagc cctcctccgg cgtcacccac ccccgcgct acgtcatcgg      120
ttacgcgctc gcgccgaaga agcagcaaag cttcatccag ccgtcgctgg tggcccaggc    180
ggcgtcgcgg ggcatggacc tcgtccccgt ggatgcgtcg cagcccctgg cagagcaagg    240
gcccttccac ctcctcatcc acaagctcta cggagacgac tggcgcgccc agctcgtggc    300
cttcgccgcg cgccacccgg ccgtccccat cgtcgacccg cccacgcca tcgaccgcct    360
ccacaaccgc atctccatgc tccaggtcgt ctccgagctc gaccacgccg ccgaccagga    420
cagcactttc ggtatcccca gccaggtcgt cgtctacgac gctgccgcgc tcgccgactt    480
cggactcctt gccgcgctcc gcttcccgct catcgccaag cccctcgtcg ccgacggcac    540
cgccaagtcc cacaagatgt cgctcgtcta ccaccgcgag ggcctcggca agctccgccc    600
gccgcttgtg ctccaggagt tcgtcaacca tggcggcgtc atcttcaagg tctacgtcgt    660
cggcggccac gtcacttgcg tcaagcgccg tagcctgccc gacgtgtccc ccgaggatga    720
cgcatcggcc cagggatccg tctccttctc ccaggtctcc aacctcccca ctgagcgcac    780
ggcggaggag tactacggcg aaaagagtct cgaggacgcc gtcgtgccgc cgccgcatt    840
catcaaccag atcgcgggcg gcctccgccg cgcgctgggc ctgcaactct tcaacttcga    900
catgatccgc gacgtccgcg ccggcgaccg ctatctcgtc attgacatca actacttccc    960
gggctacgcc aagatgccag gatacgagac tgtcctcacg gatttcttct gggagatggt    1020
ccataaggac ggcgtgggca accaacagga ggagaaaggg gccaaccatg ttgtcgtgaa    1080
ataagatgat gattgatggc actggatatc tggcgaatgc tgctgattct ggatgcagaa    1140
ttcgatgagg ggatttagtt ggttgtagta tctggcgaat gctgctggtt ctggatgcag    1200
aatttgatga ggggatttag ttggatttca acccatagca tgccgaggac ctcctagctc    1260
tttccaaacc agttgtttag gtatcttttc tgggtaagtc agcttcatct agtttagtct    1320
gtctgaacaa aagagtggga catgacccaa acggaattct aatgaaaaac gagctctcta    1380
tctgcaaaaa aaaaaaaaa aaaaaaaaa aaaaaaaaa aaaaaaaa                    1428

<210> SEQ ID NO 6
<211> LENGTH: 342
<212> TYPE: PRT
<213> ORGANISM: Zea mays

<400> SEQUENCE: 6

Met Ala Ser Asp Ala Ala Ala Glu Pro Ser Ser Gly Val Thr His Pro
 1               5                  10                  15

Pro Arg Tyr Val Ile Gly Tyr Ala Leu Ala Pro Lys Lys Gln Gln Ser
                20                  25                  30

Phe Ile Gln Pro Ser Leu Val Ala Gln Ala Ala Ser Arg Gly Met Asp
            35                  40                  45

Leu Val Pro Val Asp Ala Ser Gln Pro Leu Ala Glu Gln Gly Pro Phe
        50                  55                  60

His Leu Leu Ile His Lys Leu Tyr Gly Asp Asp Trp Arg Ala Gln Leu
65                  70                  75                  80

Val Ala Phe Ala Ala Arg His Pro Ala Val Pro Ile Val Asp Pro Pro
                85                  90                  95
```

```
His Ala Ile Asp Arg Leu His Asn Arg Ile Ser Met Leu Gln Val Val
            100                 105                 110

Ser Glu Leu Asp His Ala Ala Asp Gln Asp Ser Thr Phe Gly Ile Pro
        115                 120                 125

Ser Gln Val Val Val Tyr Asp Ala Ala Leu Ala Asp Phe Gly Leu
    130                 135                 140

Leu Ala Ala Leu Arg Phe Pro Leu Ile Ala Lys Pro Leu Val Ala Asp
145                 150                 155                 160

Gly Thr Ala Lys Ser His Lys Met Ser Leu Val Tyr His Arg Glu Gly
                165                 170                 175

Leu Gly Lys Leu Arg Pro Pro Leu Val Leu Gln Glu Phe Val Asn His
            180                 185                 190

Gly Gly Val Ile Phe Lys Val Tyr Val Gly Gly His Val Thr Cys
        195                 200                 205

Val Lys Arg Arg Ser Leu Pro Asp Val Ser Pro Glu Asp Asp Ala Ser
    210                 215                 220

Ala Gln Gly Ser Val Ser Phe Ser Gln Val Ser Asn Leu Pro Thr Glu
225                 230                 235                 240

Arg Thr Ala Glu Glu Tyr Tyr Gly Glu Lys Ser Leu Glu Asp Ala Val
                245                 250                 255

Val Pro Pro Ala Ala Phe Ile Asn Gln Ile Ala Gly Gly Leu Arg Arg
            260                 265                 270

Ala Leu Gly Leu Gln Leu Phe Asn Phe Asp Met Ile Arg Asp Val Arg
        275                 280                 285

Ala Gly Asp Arg Tyr Leu Val Ile Asp Ile Asn Tyr Phe Pro Gly Tyr
    290                 295                 300

Ala Lys Met Pro Gly Tyr Glu Thr Val Leu Thr Asp Phe Phe Trp Glu
305                 310                 315                 320

Met Val His Lys Asp Gly Val Gly Asn Gln Gln Glu Glu Lys Gly Ala
                325                 330                 335

Asn His Val Val Val Lys
            340

<210> SEQ ID NO 7
<211> LENGTH: 5344
<212> TYPE: DNA
<213> ORGANISM: Artificial Sequence
<220> FEATURE:
<221> NAME/KEY: promoter
<222> LOCATION: (266)...(1667)
<223> OTHER INFORMATION: Glb-1 promoter
<220> FEATURE:
<221> NAME/KEY: promoter
<222> LOCATION: (3191)...(4065)
<223> OTHER INFORMATION: OLE promoter
<220> FEATURE:
<221> NAME/KEY: 5'UTR
<222> LOCATION: (1707)...(1846)
<223> OTHER INFORMATION: MI1PS3 5'UTR
<221> NAME/KEY: 5'UTR
<222> LOCATION: (2892)...(3031)
<223> OTHER INFORMATION: MI1PS3 5'UTR
<220> FEATURE:
<223> OTHER INFORMATION: Expression vector

<400> SEQUENCE: 7
aacactgata gtttaaactg aaggcgggaa acgacaatct gatcatgagc ggagaattaa    60
gggagtcacg ttatgacccc cgccgatgac gcgggacaag ccgttttacg tttggaactg   120
acagaaccgc aacgttgaag gagccactca gcaagctggt acgattgtaa tacgactcac   180
```

```
tatagggcga attgagcgct gtttaaacgc tcttcaactg aagagcggt  tacccggacc   240 ggaattcgag tcgacggtat cgataagctt gccgagtgcc atccttggac actcgataaa   300
gtatatttta tttttttat  tttgccaacc aaacttttg  tggtatgttc ctacactatg   360
tagatctaca tgtaccattt tggcacaatt acatatttac aaaaatgttt tctataaata   420
ttagatttag ttcgtttatt tgaatttctt cggaaaattc acatttaaac tgcaagtcac   480
tcgaaacatg gaaaaccgtg catgcaaaat aaatgatatg catgttatct agcacaagtt   540
acgaccgatt tcagaagcag accagaatct tcaagcacca tgctcactaa acatgaccgt   600
gaacttgtta tctagttgtt taaaaattgt ataaaacaca aataaagtca gaaattaatg   660
aaacttgtcc acatgtcatg atatcatata tagaggttgt gataaaaatt tgataatgtt   720
tcggtaaagt tgtgacgtac tatgtgtaga acctaagtg  acctacacat aaaatcatag   780
agtttcaatg tagttcactc gacaaagact ttgtcaagtg tccgataaaa agtactcgac   840
aaagaagccg ttgtcgatgt actgttcgtc gagatctctt tgtcgagtgt cacactaggc   900 aaagtctttta cggagtgttt ttcaggcttt gacactcggc aaagcgctcg attccagtag   960
tgacagtaat ttgcatcaaa aatagctgag agatttaggc cccgtttcaa tctcacggga  1020
taaagtttag cttcctgcta aactttagct atatgaattg aagtgctaaa gtttagtttc  1080
aattaccacc attagctctc ctgtttagat tacaaatggc taaaagtagc taaaaaatag  1140
ctgctaaagt ttatctcgcg agattgaaac agggccttaa aatgagtcaa ctaatagacc  1200
aactaattat tagctattag tcgttagctt ctttaatcta agctaaaacc aactaatagc  1260
ttatttgttg aattacaatt agctcaacgg aattctctgt ttttctaaaa aaaaactgcc  1320
cctctcttac agcaaattgt ccgctgcccg tcgtccagat acaatgaacg tacctagtag  1380
gaactctttt acacgctcgg tcgctcgccg cggatcggag tccccggaac acgacaccac  1440
tgtggaacac gacaaagtct gctcagaggc ggccacaccc tggcgtgcac cgagccggag  1500
cccggataag cacggtaagg agagtacggc gggacgtggc gacccgtgtg tctgctgcca  1560
cgcagccttc ctccacgtag ccgcgcggcc gcgccacgta ccagggcccg gcgctggtat  1620
aaatgcgcgc cacctccgct ttagttctgc atacagccaa cccaaggatc caacacacac  1680
ccgaggatat cacagtcgag ggtcgaccca cgcgtccggc ccaacaaagg agcgcggcgg  1740
cccctccttc cttcctccca cttctctcgc gcggcgctcg cttacctcgc ctcgcattcc  1800
gttcgagcag gggagcggca gtgagaaggg agggaattaa ggcaagatgt tcatcgagag  1860
cttccgcgtc gagagccccc acgtgcgta  cggcccgacg gagatcgagt cggagtaccg  1920
gtacgacacg acggagctgg tgcacgaggc caaggacggc gcctcccgct gggtcgtccg  1980
ccccaagtcc gtcaagtaca acttccggac cagcaccgcg gtcccccaagc tcgggggtcat  2040 gcttgtgggg tggggaggca acaacgggtc cacgctgacg gctggggtca ttgccaacag  2100
ggaggggatc tcatgggcga ccaaggacaa ggtgcagcaa gccaactact acggctcccct  2160 cacccaggct tccaccatca gagtaggcag ctacaacggg gaggagatat atgcgccgtt  2220
caagagcctc ctacccatgg tgaacccaga cgaccttgtg tttggaggct gggacatcag  2280
cagcatgaac ctggcagatg ccatgaccag ggccaaggtg ctggacattg acctgcagaa  2340
gcagctcagg ccctacatgg agtccatggt gccacttccc ggtgtctatg atccggactt  2400
catcgccgct aaccagggct ctcgtgccaa caatgtcatc aagggcacca agaaagaaca  2460
ggtggagcag atcatcaaag atgatccaat ctagaaacca tgggtaggag gctcttgaac  2520
ggcgcatata tctcctcccc gttgtagctg cctactctga tggtggaagc ctgggtgagg  2580
```

```
gagccgtagt agttggcttg ctgcaccttg tccttggtcg cccatgagat cccctccctg    2640
ttggcaatga ccccagccgt cagcgtggac ccgttgttgc ctccccaccc cacaagcatg    2700
accccgagct tggggaccgc ggtgctggtc cggaagttgt acttgacgga cttggggcgg    2760
acgacccagc gggaggcgcc gtccttggcc tcgtgcacca gctccgtcgt gtcgtaccgg    2820
tactccgact cgatctccgt cgggccgtac cgcacgtggg ggctctcgac gcggaagctc    2880
tcgatgaaca tcttgcctta attccctccc ttctcactgc cgctcccctg ctcgaacgga    2940
atgcgaggcg aggtaagcga gcgccgcgcg agagaagtgg gaggaaggaa ggaggggccg    3000
ccgcgctcct ttgttgggcc ggacgcgtgg gtcgacctgc agaagcttcg gtccgggtca    3060
cctttgtcca ccaagatgga actgcggccg ctcattaatt aagtcaggcg cgcctctagt    3120
tgaagacacg ttcatgtctt catcgtaaga agacactcag tagtcttcgg ccagaatggc    3180
cgaattcgag gatccgattg actatctcat tcctccaaac ccaaacacct caaatatatc    3240
tgctatcggg attggcattc ctgtatccct acgcccgtgt accccctgtt tagagaacct    3300
cccaaggtat aagatggcga agattattgt tgtcttgtct ttcatcatat atcgagtctt    3360
tccctaggat attattattg gcaatgagca ttacacggtt aatcgattga gagaacatgc    3420
atctcacctt cagcaaataa ttacgataat ccatatttta cgcttcgtaa cttctcatga    3480
gtttcgatat acaaatttgt tttctggaca ccctaccatt catcctcttc ggagaagaga    3540
ggaagtgtcc tcaatttaaa tatgttgtca tgctgtagtt cttcacccaa tctcaacagg    3600
taccaagcac attgtttcca caaattatat tttagtcaca ataaatctat attattatta    3660
atatactaaa actatactga cgctcagatg ctttttactag ttcttgctag tatgtgatgt    3720
aggtctacgt ggaccagaaa atagtgagac acgaagacaa aaagaagtaa aagaggcccg    3780
gactacggcc cacatgagat tcggccccgc cacctccggc aaccagcggc cgatccaacg    3840
gaagtgcgcg cacacacaca acctcgtata tatcgccgcg cggaagcggc gcgaccgagg    3900
aagccttgtc ctcgacaccc cctacacagg tgtcgcgctg cccccgacac gagtcccgca    3960
tgcgtcccac gcggccgcgc cagatcccgc ctccgcgcgt tgccacgccc tctataaaca    4020
cccagctctc cctcgccctc atctacctca ctcgtagtcg tagctcgaaa ttcgatatcg    4080
gatccatgga gatctgtcga ctctagaccc gggtggatcc aatctagaaa ccatggaagg    4140
taccaagatg gccgcggaag gaagggtgca cttgttctcc ttggccacca ggtacatgta    4200
gtcgtcgtgg ccccatgaca tgagcacctt gttgaggccg cagccctccg agtagacccc    4260
caacttggtg ttgagcttcg ggttgtggta gtcggggttc tccttgaagt acttgaagtg    4320
gacgttgcac tcgtcgtatg cgcagccgac ggggaaggtg tcaccgacga cagcccactg    4380
agggagctcc ccgaagcttg ggtgcagcag caccttgccc aggtcgtgga tgagtccggt    4440
gaggtggagc cagtcctcgt cggggtagtc cttgcggatg gcctcggcgg tctgcagcag    4500
gtgctcgatc tggggcatgt ccaggtccgg gtcgctgtcg tcgatgaact cgttcagcag    4560
ctcgatgcac tcccagatgc ccatctccgt cttgtccagc cgcccgtact ccgcccgcat    4620
ccgcgccacg aactcgtgcg tctgcctcac gtggttcacc cggtagaact cctctaccgt    4680
ctgcttccgc tccgactccg cgtcgtagtc cctgaaggta ttgccgaagg cgttggcgtc    4740
cggcacgacg aagccggcgt cgagcaccag ctccgcggac cgaattcgag gtgaggcaga    4800
cgcacgagtt cgtggcgcgg atgcgggcgg agtacgggcg gctggacaag acggagatgg    4860
gcatctggga gtgcatcgag ctgctgaacg agttcatcga cgacagcgac ccggacctgg    4920
```

-continued

| | | | |
|---|---|---|---|
| acatgcccca gatcgagcac ctgctgcaga ccgccgaggc catccgcaag gactaccccg | | | 4980 |
| acgaggactg gctccacctc accggactca tccacgacct gggcaaggtg ctgctgcacc | | | 5040 |
| caagcttcgg ggagctccct cagtgggctg tcgtcggtga caccttcccc gtcggctgcg | | | 5100 |
| catacgacga gtgcaacgtc cacttcaagt ctcgagccca tcaaccgcgg aaagatctaa | | | 5160 |
| gcatgcaagg gccccggccg aagcttggcc tagaaggcca tttaaatcct gaggatctgg | | | 5220 |
| tcttcctaag gacccgggcg gtccgattaa actttaattc ggaccgaagc ttctgcagga | | | 5280 |
| attcctgcag tgcagcgtga cccggtcgtg cccctctcta gtggatctga gcttctagaa | | | 5340 |
| atac | | | 5344 |

<210> SEQ ID NO 8
<211> LENGTH: 4115
<212> TYPE: DNA
<213> ORGANISM: Artificial Sequence
<220> FEATURE:
<221> NAME/KEY: CDS
<222> LOCATION: (1658)...(2575)
<223> OTHER INFORMATION: ZM-MIOX
<220> FEATURE:
<221> NAME/KEY: CDS
<222> LOCATION: (3147)...(4064)
<223> OTHER INFORMATION: ZM-MIOX
<220> FEATURE:
<221> NAME/KEY: intron
<222> LOCATION: (2600)...(3136)
<223> OTHER INFORMATION: ADH1 intron
<221> NAME/KEY: promoter
<222> LOCATION: (1)...(1652)
<223> OTHER INFORMATION: ZM-40 promoter
<220> FEATURE:
<221> NAME/KEY: variation
<222> LOCATION: (1022)...(1022)
<223> OTHER INFORMATION: Expression vector
<220> FEATURE:
<223> OTHER INFORMATION: n = any nucleotide

<400> SEQUENCE: 8

| | | | |
|---|---|---|---|
| gaccggaatt cgagctcggt acccagctta gctagatcat ttgtaagaat gcaacttgtt | | | 60 |
| catatagcat ggctacagcc tacatcatct gaaatagacc tgtttatagg atacctaagc | | | 120 |
| tcaattcacc ctatatctaa aacctacgag gcctaaacac acccgtcctc aagaaaacga | | | 180 |
| ccagaccaaa ccaaaccatg cgtccgcgtc atggttttgt agacacgttt acgtatcaat | | | 240 |
| tatagtgttc tgattttat attctcctaa ttatttagag ctaaatttat ttttatgata | | | 300 |
| gcagagatct aaatatttt gttttgattt tttatatact aaaatcatct ctacaatatt | | | 360 |
| agagatttta aatgctcaga agaattttac ttgaattaaa accttactg attttaact | | | 420 |
| aaaacggaga tcaaaagaaa tctatccaag gctgcctcta agagccttcg tgtctcgttt | | | 480 |
| tcttatttca gacttcactc atcttcttat ttcaggctcc actatataag gtggtctcta | | | 540 |
| gtatcttcc tatcacatat cctatttaaa actttagtat ataaaacatt ataattcata | | | 600 |
| atataaatcg attatttac acgatctcag cctaaaagcg gtaatatgca cgctctgagc | | | 660 |
| atggcccaag ctccacgtta accgttctgt caaaaaaaaa aacatctagt ctagaatgga | | | 720 |
| aaacacacga ttttagaagt taggactagt ttggcaactc aattttccaa atgattctca | | | 780 |
| ttcttttaag aggatttaat ttattttttg gtaaaatagg aatcactaga aactctattt | | | 840 |
| tttcaagaga agtaagcta ttttttaga aaaataaaaa atcccttaaa aaatattgtt | | | 900 |
| cgtaaattag ccctaagatg gactaaaaat ctggttttat agaatagggga gggatcgagc | | | 960 |
| aaccgccaaa tctacgcgcc aaaaaggtac cttttccgtg aataaacacg actgcggcga | | | 1020 |

```
tnacgatctg atcgaactcc gtagaataaa atggagcagc ggaatagtgt gggaagcaca    1080
agcaccagga ggagctgaaa ccgaaccgaa gtggcgaaca gatccccact ccggccggca    1140
cccgagtgtg cgagacgtgt ggggctgatc tgacgagcct ggaagaagaa gaagaaaaaa    1200
aagtcctcac gctcctgctt ggctccatcg acagctcact agctgttacc ggatgctcgc    1260
gtctctggtg cctctcgatt catcatccat cgttggtggc ggcggcgggg cggcaaaggt    1320
tctgattccg cagcagccaa gtgctcctcc tgcagacgaa aatgacggca gaggttggcg    1380
ttgatccagg agactcatca gtttagttta ataatgaatc tgtagcaggc gcttcagtct    1440
ctcatcggat gagcgagcag cttagcgagg caggtggtgg tccctggctc gcccacgtcc    1500
attctttccc gcccgtcctg ccgtccactc cgccgcctat ttatacccct cctcgcccac    1560
cctgccatcc tcaccatcgc aattcacaag caaagcaatc agagccaagc acccaccgtc    1620
ctcctttctt tccttcgact catcaaagcc gggatccatg acgatcacca ttgaacagcc    1680
ccagctcgat gcggtggcgg agaggaaagt ccccggcgga ggtgacccog cggagctggt    1740 gctcgacgcc ggcttcgtcg tgccggacgc caacgccttc ggcaatacct tcagggacta    1800
cgacgcggag tcggagcgga agcagacggt agaggagttc taccgggtga accacgtgag    1860
gcagacgcac gagttcgtgg cgcggatgcg ggcggagtac gggcggctgg acaagacgga    1920
gatgggcatc tgggagtgca tcgagctgct gaacgagttc atcgacgaca gcgacccgga    1980
cctggacatg ccccagatcg agcacctgct gcagaccgcc gaggccatcc gcaaggacta    2040
ccccgacgag gactggctcc acctcaccgg actcatccac gacctgggca aggtgctgct    2100
gcacccaagc ttcggggagc tccctcagtg ggctgtcgtc ggtgacacct tccccgtcgg    2160
ctgcgcatac gacgagtgca acgtccactt caagtacttc aaggagaacc ccgactacca    2220
caacccgaag ctcaacacca gttgggggt ctactcggag ggctgcggcc tcaacaaggt    2280
gctcatgtca tggggccacg acgactacat gtacctggtg gccaaggaga acaagtgcac    2340
ccttccttcc gcggggctgt tcatcatcag ataccactcg ttctaccccc tgcacaagca    2400
tggagcctac acacacctga tggacgatga ggacaaggag aacctcaagt ggctgcatgt    2460
gttcaacaag tatgacctgt acagcaagag caacagcagg atcgacgtgg aggaggtgaa    2520
gccctactac atgtccctaa tcgacaagta cttcccggcc aagctaagat ggtgacccat    2580
ctgcagtcga cgtgcaaagg tccgccttgt ttctcctctg tctcttgatc tgactaatct    2640
tggtttatga ttcgttgagt aattttgggg aaagcttcgt ccacagtttt ttttcgatga    2700
acagtgccgc agtggcgctg atcttgtatg ctatcctgca atcgtggtga acttatttct    2760
tttatatcct ttactccat gaaaaggcta gtaatctttc tcgatgtaac atcgtccagc    2820
actgctatta ccgtgtggtc catccgacag tctggctgaa cacatcatac gatctatgga    2880
gcaaaaatct atcttccctg ttctttaatg aaggacgtca ttttcattag tatgatctag    2940
gaatgttgca acttgcaagg aggcgttctt ttctttgaat ttaactaact cgttgagtgg    3000 ccctgttct cggacgtaag gcctttgctg ctccacacat gtccattcga atttaccgt     3060 gtttagcaag ggcgaaaagt ttgcatcttg atgatttagc ttgactatgc gattgctttc    3120
ctggacccgt gcagctggat cccgggtcac catcttagct tggccgggaa gtacttgtcg    3180
attagggaca tgtagtaggg cttcacctcc tccacgtcga tcctgctgtt gctcttgctg    3240
tacaggtcat acttgttgaa cacatgcagc cacttgaggt tctccttgtc ctcatcgtcc    3300
atcaggtgtg tgtaggctcc atgcttgtgc aggggggtaga acgagtggta tctgatgatg    3360
aacagccccg cggaaggaag ggtgcacttg ttctccttgg ccaccaggta catgtagtcg    3420
```

-continued

| | |
|---|---|
| tcgtggcccc atgacatgag caccttgttg aggccgcagc cctccgagta gaccccaac | 3480 |
| ttggtgttga gcttcgggtt gtggtagtcg gggttctcct tgaagtactt gaagtggacg | 3540 |
| ttgcactcgt cgtatgcgca gccgacgggg aaggtgtcac cgacgacagc ccactgaggg | 3600 |
| agctccccga agcttgggtg cagcagcacc ttgcccaggt cgtggatgag tccggtgagg | 3660 |
| tggagccagt cctcgtcggg gtagtccttg cggatggcct cggcggtctg cagcaggtgc | 3720 |
| tcgatctggg gcatgtccag gtccgggtcg ctgtcgtcga tgaactcgtt cagcagctcg | 3780 |
| atgcactccc agatgcccat ctccgtcttg tccagccgcc cgtactccgc ccgcatccgc | 3840 |
| gccacgaact cgtgcgtctg cctcacgtgg ttcacccggt agaactcctc taccgtctgc | 3900 |
| ttccgctccg actccgcgtc gtagtccctg aaggtattgc cgaaggcgtt ggcgtccggc | 3960 |
| acgacgaagc cggcgtcgag caccagctcc gcggggtcac ctccgccggg gactttcctc | 4020 |
| tccgccaccg catcgagctg ggctgttca atggtgatcg tcatggatcc aagcttggtc | 4080 |
| acccggtccg ggcctagaag gccgatctcc cgggc | 4115 |

<210> SEQ ID NO 9
<211> LENGTH: 4060
<212> TYPE: DNA
<213> ORGANISM: Artificial Sequence
<220> FEATURE:
<221> NAME/KEY: CDS
<222> LOCATION: (1596)...(2513)
<223> OTHER INFORMATION: ZM-MIOX
<220> FEATURE:
<221> NAME/KEY: CDS
<222> LOCATION: (3085)...(4002)
<223> OTHER INFORMATION: ZM-MIOX
<220> FEATURE:
<221> NAME/KEY: intron
<222> LOCATION: (2538)...(3074)
<223> OTHER INFORMATION: ADH1 intron
<221> NAME/KEY: promoter
<222> LOCATION: (74)...(1590)
<223> OTHER INFORMATION: Maize gamma zein promoter
<220> FEATURE:
<223> OTHER INFORMATION: Expression vector

<400> SEQUENCE: 9

| | |
|---|---|
| tccggccaga atggcccgga ccgggttacc cggtccggaa ttcgagctcc accgcggtgg | 60 |
| cggccgctct agattatata atttataagc tgaaacaacc cggccctaaa gcactatcgt | 120 |
| atcacctatc tgaaataagt cacgggtttc gaacgtccac ttgcgtcgca cggaattgca | 180 |
| tgtttcttgt tggaagcata ttcacgcaat ctccacacat aaaggtttat gtataaactt | 240 |
| acatttagct cagtttaatt acagtcttat ttggatgcat atgtatggtt ctcaatccat | 300 |
| ataagttaga gtaaaaaata agtttaaatt ttatcttaat tcactccaac atatatggat | 360 |
| tgagtacaat actcatgtgc atccaaacaa actacttata ttgaggtgaa tttggataga | 420 |
| aattaaacta acttacacac taagccaatc tttactatat aaagcacca gtttcaacga | 480 |
| tcgtcccgcg tcaatattat taaaaaactc ctacatttct ttataatcaa cccgcactct | 540 |
| tataatctct tctctactac tataataaga gagtttatgt acaaaataag gtgaaattat | 600 |
| gtataagtgt tctggatatt ggttgttggc tccatattca cacaacctaa tcaatagaaa | 660 |
| acatatgttt tattaaaaca aaatttatca tatatcatat atatatatat acatatatat | 720 |
| atataaaccg tagcaatgca cggcatatata actagtgcaa cttaatacat gtgtgtatta | 780 |
| agatgaataa gagggtatcc aaataaaaaa cttgttcgct tacgtctgga tcgaaagggg | 840 |
| ttggaaacga ttaaatctct tcctagtcaa aattgaatag aaggagattt aatctctccc | 900 |

```
aatccccttc gatcatccag gtgcaaccgt ataagtccta aagtggtgag gaacacgaaa    960
caaccatgca ttggcatgta aagctccaag aatttgttgt atccttaaca actcacagaa   1020
catcaaccaa aattgcacgt caagggtatt gggtaagaaa caatcaaaca aatcctctct   1080
gtgtgcaaag aaacacggtg agtcatgccg agatcatact catctgatat acatgcttac   1140
agctcacaag acattacaaa caactcatat tgcattacaa agatcgtttc atgaaaaata   1200
aaataggccg gacaggacaa aaatccttga cgtgtaaagt aaatttacaa caaaaaaaaa   1260
gccatatgtc aagctaaatc taattcgttt tacgtagatc aacaacctgt agaaggcaac   1320
aaaactgagc cacgcagaag tacagaatga ttccagatga accatcgacg tgctacgtaa   1380
agagagtgac gagtcatata catttggcaa gaaaccatga agctgcctac agccgtctcg   1440
gtggcataag aacacaagaa attgtgttaa ttaatcaaag ctataaataa cgctcgcatg   1500
cctgtgcact tctccatcac caccactggg tcttcagacc attagcttta tctactccag   1560
agcgcagaag aacccgatcg acagatatcg gatccatgac gatcaccatt gaacagcccc   1620
agctcgatgc ggtggcggag aggaaagtcc ccggcggagg tgaccccgcg gagctggtgc   1680
tcgacgccgg cttcgtcgtg ccggacgcca acgccttcgg caataccttc agggactacg   1740
acgcggagtc ggagcggaag cagacggtag aggagttcta ccgggtgaac cacgtgaggc   1800
agacgcacga gttcgtggcg cggatgcggg cggagtacgg gcggctggac aagacggaga   1860
tgggcatctg ggagtgcatc gagctgctga acgagttcat cgacgacagc gacccggacc   1920
tggacatgcc ccagatcgag cacctgctgc agaccgccga ggccatccgc aaggactacc   1980
ccgacgagga ctggctccac ctcaccggac tcatccacga cctgggcaag gtgctgctgc   2040
acccaagctt cggggagctc cctcagtggg ctgtcgtcgg tgacaccttc cccgtcggct   2100
gcgcatacga cgagtgcaac gtccacttca gtacttcaa ggagaacccc gactaccaca   2160
acccgaagct caacaccaag ttgggggtct actcggaggg ctgcggcctc aacaaggtgc   2220
tcatgtcatg gggccacgac gactacatgt acctggtggc caaggagaac aagtgcaccc   2280
ttccttccgc ggggctgttc atcatcagat accactcgtt ctaccccctg cacaagcatg   2340
gagcctacac acacctgatg gacgatgagg acaaggagaa cctcaagtgg ctgcatgtgt   2400
tcaacaagta tgacctgtac agcaagagca acagcaggat cgacgtggag gaggtgaagc   2460
cctactacat gtccctaatc gacaagtact tcccggccaa gctaagatgg tgacccatct   2520
gcagtcgacg tgcaaaggtc cgccttgttt ctcctctgtc tcttgatctg actaatcttg   2580
gtttatgatt cgttgagtaa ttttggggaa agcttcgtcc acagttttt ttcgatgaac   2640
agtgccgcag tggcgctgat cttgtatgct atcctgcaat cgtggtgaac ttatttcttt   2700
tatatccttt actcccatga aaaggctagt aatctttctc gatgtaacat cgtccagcac   2760
tgctattacc gtgtggtcca tccgacagtc tggctgaaca catcatacga tctatggagc   2820
aaaaatctat cttccctgtt ctttaatgaa ggacgtcatt ttcattagta tgatctagga   2880
atgttgcaac ttgcaaggag gcgtttcttt ctttgaattt aactaactcg ttgagtggcc   2940
ctgtttctcg gacgtaaggc ctttgctgct ccacacatgt ccattcgaat tttaccgtgt   3000
ttagcaaggg cgaaaagttt gcatcttgat gatttagctt gactatgcga ttgctttcct   3060
ggacccgtgc agctggatcc cgggtcacca tcttagcttg gcgggaagt acttgtcgat   3120
tagggacatg tagtagggct tcacctcctc cacgtcgatc ctgctgttgc tcttgctgta   3180
caggtcatac ttgttgaaca catgcagcca cttgaggttc tccttgtcct catcgtccat   3240
```

-continued

```
caggtgtgtg taggctccat gcttgtgcag ggggtagaac gagtggtatc tgatgatgaa    3300
cagccccgcg gaaggaaggg tgcacttgtt ctccttggcc accaggtaca tgtagtcgtc    3360
gtggccccat gacatgagca ccttgttgag gccgcagccc tccgagtaga cccccaactt    3420
ggtgttgagc ttcgggttgt ggtagtcggg gttctccttg aagtacttga agtggacgtt    3480
gcactcgtcg tatgcgcagc cgacggggaa ggtgtcaccg acgacagccc actgagggag    3540
ctccccgaag cttgggtgca gcagcacctt gcccaggtcg tggatgagtc cggtgaggtg    3600
gagccagtcc tcgtcggggt agtccttgcg gatggcctcg gcggtctgca gcaggtgctc    3660
gatctggggc atgtccaggt ccgggtcgct gtcgtcgatg aactcgttca gcagctcgat    3720
gcactcccag atgcccatct ccgtcttgtc cagccgcccg tactccgccc gcatccgcgc    3780
cacgaactcg tgcgtctgcc tcacgtggtt cacccggtag aactcctcta ccgtctgctt    3840
ccgctccgac tccgcgtcgt agtccctgaa ggtattgccg aaggcgttgg cgtccggcac    3900
gacgaagccg gcgtcgagca ccagctccgc ggggtcacct ccgccgggga ctttcctctc    3960
cgccaccgca tcgagctggg gctgttcaat ggtgatcgtc atggatccaa gcttcggacc    4020
gggtcacccg gtccgggcct agaaggccga tctcccgggc                          4060
```